(12) United States Patent
Van Hoven et al.

(10) Patent No.: US 11,534,303 B2
(45) Date of Patent: Dec. 27, 2022

(54) DEVICES AND SYSTEMS FOR ACCESSING AND REPAIRING A HEART VALVE

(71) Applicant: EVALVE, INC., Santa Clara, CA (US)

(72) Inventors: Dylan T. Van Hoven, San Carlos, CA (US); Michael F. Wei, Redwood City, CA (US)

(73) Assignee: EVALVE, INC., Santa Clara, CA (US)

( * ) Notice: Subject to any disclaimer, the term of this patent is extended or adjusted under 35 U.S.C. 154(b) by 0 days.

(21) Appl. No.: 17/067,555

(22) Filed: Oct. 9, 2020

(65) Prior Publication Data

US 2021/0315695 A1    Oct. 14, 2021

Related U.S. Application Data

(60) Provisional application No. 63/007,854, filed on Apr. 9, 2020.

(51) Int. Cl.
*A61F 2/24*    (2006.01)

(52) U.S. Cl.
CPC ............ *A61F 2/2466* (2013.01); *A61F 2/246* (2013.01); *A61F 2/2436* (2013.01); *A61F 2/2412* (2013.01)

(58) Field of Classification Search
CPC .... A61F 2/2412; A61F 2/2466; A61F 2/2436; A61F 2/246
See application file for complete search history.

(56) References Cited

U.S. PATENT DOCUMENTS

| | | |
|---|---|---|
| 3,378,010 A | 4/1968 | Codling et al. |
| 3,874,388 A | 4/1975 | King et al. |
| 4,007,743 A | 2/1977 | Blake |
| 4,055,861 A | 11/1977 | Carpentier et al. |
| 4,327,736 A | 5/1982 | Inoue |
| 4,340,091 A | 7/1982 | Skelton et al. |
| 4,657,024 A | 4/1987 | Coneys |
| 4,693,248 A | 9/1987 | Failla |
| 4,716,886 A | 1/1988 | Schulman et al. |
| 4,795,458 A | 1/1989 | Regan |
| 4,809,695 A | 3/1989 | Gwathmey et al. |
| 4,930,674 A | 6/1990 | Barak |
| 5,002,562 A | 3/1991 | Oberlander |

(Continued)

FOREIGN PATENT DOCUMENTS

| | | |
|---|---|---|
| CA | 2 296 317 C | 1/2009 |
| DE | 10 2017 118 468 A1 | 2/2019 |

(Continued)

OTHER PUBLICATIONS

U.S. Appl. No. 16/882,038 (US 2020/0367871), filed May 22, 2020 (Nov. 26, 2020).

(Continued)

*Primary Examiner* — Suba Ganesan

(74) *Attorney, Agent, or Firm* — Baker Botts L.L.P.

(57) ABSTRACT

Medical delivery system for accessing a tricuspid valve via an inferior vena cava, including an outer guide catheter, an inner guide catheter and an interventional catheter. The first deflection portion of the outer guide catheter is steerable to define a first outer-guide-catheter curve and the second deflection portion of the outer guide catheter is steerable to define a second outer-guide-catheter curve and the first deflection portion of the inner guide catheter is steerable to define a first inner-guide-catheter curve.

19 Claims, 20 Drawing Sheets

(56) References Cited

U.S. PATENT DOCUMENTS

| | | |
|---|---|---|
| 5,069,679 A | 12/1991 | Taheri |
| 5,098,440 A | 3/1992 | Hillstead |
| 5,125,895 A | 6/1992 | Buchbinder et al. |
| 5,147,370 A | 9/1992 | McNamara et al. |
| 5,171,259 A | 12/1992 | Inoue |
| 5,222,963 A | 6/1993 | Brinkerhoff et al. |
| 5,271,544 A | 12/1993 | Fox et al. |
| 5,327,905 A | 7/1994 | Avitall |
| 5,330,501 A | 7/1994 | Tovey et al. |
| 5,334,217 A | 8/1994 | Das |
| 5,363,861 A | 11/1994 | Edwards et al. |
| 5,389,077 A | 2/1995 | Melinyshyn et al. |
| 5,403,326 A | 4/1995 | Harrison et al. |
| 5,425,744 A | 6/1995 | Fagan et al. |
| 5,450,860 A | 9/1995 | O'Connor |
| 5,452,837 A | 9/1995 | Williamson, IV et al. |
| 5,456,400 A | 10/1995 | Shichman et al. |
| 5,456,674 A | 10/1995 | Bos et al. |
| 5,478,353 A | 12/1995 | Yoon |
| 5,542,949 A | 8/1996 | Yoon |
| 5,562,678 A | 10/1996 | Booker |
| 5,601,224 A | 2/1997 | Bishop et al. |
| 5,601,574 A | 2/1997 | Stefanchik et al. |
| 5,607,445 A | 3/1997 | Summers |
| 5,607,462 A | 3/1997 | Imran |
| 5,607,471 A | 3/1997 | Seguin et al. |
| 5,609,598 A | 3/1997 | Laufer et al. |
| 5,611,794 A | 3/1997 | Sauer et al. |
| 5,636,634 A | 6/1997 | Kordis et al. |
| 5,656,011 A | 8/1997 | Uihlein et al. |
| 5,695,504 A | 12/1997 | Gifford, III et al. |
| 5,713,911 A | 2/1998 | Racenet et al. |
| 5,716,417 A | 2/1998 | Girard et al. |
| 5,741,297 A | 4/1998 | Simon |
| 5,755,778 A | 5/1998 | Kleshinski |
| 5,782,239 A | 7/1998 | Webster, Jr. |
| 5,797,960 A | 8/1998 | Stevens et al. |
| 5,810,847 A | 9/1998 | Laufer et al. |
| 5,814,097 A | 9/1998 | Sterman et al. |
| 5,843,178 A | 12/1998 | Vanney et al. |
| 5,849,019 A | 12/1998 | Yoon |
| 5,855,601 A | 1/1999 | Bessler et al. |
| 5,924,424 A | 7/1999 | Stevens et al. |
| 5,976,159 A | 11/1999 | Bolduc et al. |
| 6,015,417 A | 1/2000 | Reynolds, Jr. |
| 6,048,351 A | 4/2000 | Gordon et al. |
| 6,079,414 A | 6/2000 | Roth |
| 6,117,144 A | 9/2000 | Nobles et al. |
| 6,120,496 A | 9/2000 | Whayne et al. |
| 6,129,758 A | 10/2000 | Love |
| 6,149,658 A | 11/2000 | Gardiner et al. |
| 6,165,183 A | 12/2000 | Kuehn et al. |
| 6,182,664 B1 | 2/2001 | Cosgrove |
| 6,193,734 B1 | 2/2001 | Bolduc et al. |
| 6,200,315 B1 | 3/2001 | Gaiser et al. |
| 6,217,528 B1 | 4/2001 | Koblish et al. |
| 6,269,819 B1 | 8/2001 | Oz et al. |
| 6,290,674 B1 | 9/2001 | Roue et al. |
| 6,312,447 B1 | 11/2001 | Grimes |
| 6,332,880 B1 | 12/2001 | Yang et al. |
| 6,346,074 B1 | 2/2002 | Roth |
| 6,419,696 B1 | 7/2002 | Ortiz et al. |
| 6,461,366 B1 | 10/2002 | Seguin |
| 6,482,224 B1 | 11/2002 | Michler et al. |
| 6,496,420 B2 | 12/2002 | Manning |
| 6,544,215 B1 | 4/2003 | Bencini et al. |
| 6,551,303 B1 | 4/2003 | Van Tassel et al. |
| 6,575,971 B2 | 6/2003 | Hauck et al. |
| 6,599,311 B1 | 7/2003 | Biggs et al. |
| 6,626,930 B1 | 9/2003 | Allen et al. |
| 6,629,534 B1 | 10/2003 | St. Goar et al. |
| 6,669,687 B1 | 12/2003 | Saadat |
| 6,695,866 B1 | 2/2004 | Kuehn et al. |
| 6,719,767 B1 | 4/2004 | Kimblad |
| 6,752,813 B2 | 6/2004 | Goldfarb et al. |
| 6,770,083 B2 | 8/2004 | Seguin |
| 6,797,002 B2 | 9/2004 | Spence et al. |
| 6,837,867 B2 | 1/2005 | Kortelling |
| 6,855,137 B2 | 2/2005 | Bon |
| 6,875,224 B2 | 4/2005 | Grimes |
| 6,908,481 B2 | 6/2005 | Cribier |
| 6,926,730 B1 | 8/2005 | Nguyen et al. |
| 7,011,669 B2 | 3/2006 | Kimblad |
| 7,101,395 B2 | 9/2006 | Tremulis et al. |
| 7,112,207 B2 | 9/2006 | Allen et al. |
| 7,125,421 B2 | 10/2006 | Tremulis et al. |
| 7,226,467 B2 | 6/2007 | Lucatero et al. |
| 7,556,632 B2 | 7/2009 | Zadno |
| 7,563,267 B2 | 7/2009 | Goldfarb et al. |
| 7,563,273 B2 | 7/2009 | Goldfarb et al. |
| 7,569,062 B1 | 8/2009 | Kuehn et al. |
| 7,604,646 B2 | 10/2009 | Goldfarb et al. |
| 7,635,329 B2 | 12/2009 | Goldfarb et al. |
| 7,655,015 B2 | 2/2010 | Goldfarb et al. |
| 7,666,204 B2 | 2/2010 | Thornton et al. |
| 7,736,388 B2 | 6/2010 | Goldfarb et al. |
| 7,811,296 B2 | 10/2010 | Goldfarb et al. |
| 7,972,323 B1 | 7/2011 | Bencini et al. |
| 7,981,139 B2 | 7/2011 | Martin et al. |
| 8,057,493 B2 | 11/2011 | Goldfarb et al. |
| 8,062,313 B2 | 11/2011 | Kimblad |
| 8,118,822 B2 | 2/2012 | Schaller et al. |
| 8,216,230 B2 | 7/2012 | Hauck et al. |
| 8,216,256 B2 | 7/2012 | Raschdorf, Jr. et al. |
| 8,303,608 B2 | 11/2012 | Goldfarb et al. |
| 8,470,028 B2 | 6/2013 | Thornton et al. |
| 8,500,761 B2 | 8/2013 | Goldfarb et al. |
| 8,734,505 B2 | 5/2014 | Goldfarb et al. |
| 8,740,920 B2 | 6/2014 | Goldfarb et al. |
| 8,753,362 B2 | 6/2014 | Widomski et al. |
| 8,945,177 B2 | 2/2015 | Dell et al. |
| 9,011,468 B2 | 4/2015 | Ketai et al. |
| 9,180,005 B1 | 11/2015 | Lashinski et al. |
| 9,510,829 B2 | 12/2016 | Goldfarb et al. |
| 9,750,505 B2 | 9/2017 | Miles et al. |
| 9,770,232 B2 | 9/2017 | Amin et al. |
| 10,076,415 B1 | 9/2018 | Metchik et al. |
| 10,105,222 B1 | 10/2018 | Metchik et al. |
| 10,123,873 B1 | 11/2018 | Metchik et al. |
| 10,130,475 B1 | 11/2018 | Metchik et al. |
| 10,136,993 B1 | 11/2018 | Metchik et al. |
| 10,159,570 B1 | 12/2018 | Metchik et al. |
| 10,231,837 B1 | 3/2019 | Metchik et al. |
| 10,238,493 B1 | 3/2019 | Metchik et al. |
| 10,245,144 B1 | 4/2019 | Metchik et al. |
| D847,983 S | 5/2019 | Ho et al. |
| 10,314,586 B2 | 6/2019 | Greenberg et al. |
| 10,413,408 B2 | 9/2019 | Krone et al. |
| 10,507,109 B2 | 12/2019 | Metchik et al. |
| 10,517,726 B2 | 12/2019 | Chau et al. |
| 10,524,792 B2 | 1/2020 | Hernandez et al. |
| 10,595,997 B2 | 3/2020 | Metchik et al. |
| 10,646,342 B1 | 5/2020 | Marr et al. |
| 10,779,837 B2 | 9/2020 | Lee et al. |
| D902,403 S | 11/2020 | Marsot et al. |
| 10,856,988 B2 | 12/2020 | McNiven et al. |
| 2002/0013571 A1 | 1/2002 | Goldfarb et al. |
| 2002/0082585 A1 | 6/2002 | Carroll et al. |
| 2002/0183787 A1 | 12/2002 | Wahr et al. |
| 2003/0018358 A1 | 1/2003 | Saadat |
| 2003/0069593 A1 | 4/2003 | Tremulis et al. |
| 2003/0139819 A1 | 7/2003 | Beer et al. |
| 2003/0167071 A1 | 9/2003 | Martin et al. |
| 2004/0034365 A1 | 2/2004 | Lentz et al. |
| 2004/0044350 A1 | 3/2004 | Martin et al. |
| 2004/0073242 A1 | 4/2004 | Chanduszko |
| 2004/0176799 A1 | 9/2004 | Chanduszko et al. |
| 2004/0220610 A1 | 11/2004 | Kreidler et al. |
| 2005/0043759 A1 | 2/2005 | Chanduszko |
| 2005/0065548 A1 | 3/2005 | Marino et al. |
| 2005/0267493 A1 | 12/2005 | Schreck et al. |
| 2005/0273135 A1 | 12/2005 | Chanduszko et al. |
| 2005/0288786 A1 | 12/2005 | Chanduszko |
| 2006/0122646 A1 | 6/2006 | Corcoran et al. |

(56) References Cited

U.S. PATENT DOCUMENTS

| | | |
|---|---|---|
| 2006/0265004 A1 | 11/2006 | Callaghan et al. |
| 2006/0271089 A1 | 11/2006 | Alejandro et al. |
| 2007/0010851 A1 | 1/2007 | Chanduszko |
| 2007/0027533 A1 | 2/2007 | Douk |
| 2007/0038293 A1 | 2/2007 | St.Goar et al. |
| 2007/0073337 A1 | 3/2007 | Abbott et al. |
| 2007/0112380 A1 | 5/2007 | Figulla et al. |
| 2007/0167981 A1 | 7/2007 | Opolski et al. |
| 2007/0179527 A1 | 8/2007 | Eskuri et al. |
| 2007/0250081 A1 | 10/2007 | Cahill et al. |
| 2007/0260305 A1 | 11/2007 | Drews et al. |
| 2008/0287741 A1 | 11/2008 | Ostrovsky et al. |
| 2009/0163934 A1 | 6/2009 | Raschdorf et al. |
| 2009/0188964 A1 | 7/2009 | Orlov |
| 2010/0004740 A1 | 1/2010 | Seguin et al. |
| 2010/0234878 A1 | 9/2010 | Hruska et al. |
| 2010/0234885 A1 | 9/2010 | Frazier et al. |
| 2011/0022078 A1 | 1/2011 | Hinman |
| 2011/0060407 A1 | 3/2011 | Ketai et al. |
| 2011/0276086 A1 | 11/2011 | Al-Qbandi et al. |
| 2011/0307055 A1 | 12/2011 | Goldfarb et al. |
| 2012/0190924 A1 | 7/2012 | Tseng |
| 2013/0066341 A1 | 3/2013 | Ketai et al. |
| 2013/0066342 A1* | 3/2013 | Dell .............. A61B 17/083 606/151 |
| 2013/0282110 A1 | 10/2013 | Schweich, Jr. et al. |
| 2013/0289718 A1 | 10/2013 | Tsukashima et al. |
| 2013/0310928 A1 | 11/2013 | Morriss et al. |
| 2014/0005778 A1 | 1/2014 | Buchbinder et al. |
| 2014/0163669 A1 | 6/2014 | Ben-zvi et al. |
| 2014/0200662 A1 | 7/2014 | Eftel et al. |
| 2015/0066077 A1 | 3/2015 | Akpinar |
| 2015/0173765 A1 | 6/2015 | Miller et al. |
| 2016/0022417 A1 | 1/2016 | Karapetian et al. |
| 2016/0030169 A1 | 2/2016 | Shahriari |
| 2017/0042546 A1 | 2/2017 | Goldfarb et al. |
| 2017/0049455 A1 | 2/2017 | Seguin |
| 2017/0239048 A1 | 8/2017 | Goldfarb et al. |
| 2017/0265994 A1 | 9/2017 | Krone |
| 2018/0021133 A1 | 1/2018 | Barbarino |
| 2018/0036119 A1 | 2/2018 | Wei et al. |
| 2018/0055633 A1 | 3/2018 | Costello et al. |
| 2018/0092661 A1 | 4/2018 | Prabhu |
| 2018/0133010 A1 | 5/2018 | Kizuka |
| 2018/0146964 A1 | 5/2018 | Garcia et al. |
| 2018/0146966 A1 | 5/2018 | Hernández et al. |
| 2018/0235657 A1 | 8/2018 | Abunassar |
| 2018/0242976 A1 | 8/2018 | Kizuka |
| 2018/0243086 A1 | 8/2018 | Barbarino et al. |
| 2018/0325671 A1 | 11/2018 | Abunassar et al. |
| 2018/0344460 A1 | 12/2018 | Wei |
| 2018/0353181 A1 | 12/2018 | Wei |
| 2018/0360457 A1 | 12/2018 | Ellis et al. |
| 2019/0053803 A1 | 2/2019 | Ketai et al. |
| 2019/0125536 A1 | 5/2019 | Prabhu et al. |
| 2019/0142589 A1 | 5/2019 | Basude |
| 2019/0151041 A1 | 5/2019 | Ho et al. |
| 2019/0151089 A1 | 5/2019 | Wei |
| 2019/0159899 A1 | 5/2019 | Marsot et al. |
| 2019/0167197 A1 | 6/2019 | Abunassar et al. |
| 2019/0183571 A1 | 6/2019 | De Marchena |
| 2019/0209293 A1 | 7/2019 | Metchik et al. |
| 2019/0247187 A1 | 8/2019 | Kizuka |
| 2019/0274831 A1 | 9/2019 | Prabhu |
| 2019/0321597 A1 | 10/2019 | Van Hoven et al. |
| 2019/0343630 A1 | 11/2019 | Kizuka |
| 2019/0350702 A1 | 11/2019 | Hernandez |
| 2019/0350710 A1 | 11/2019 | Ketai et al. |
| 2019/0365536 A1 | 12/2019 | Prabhu |
| 2020/0000473 A1 | 1/2020 | Dell et al. |
| 2020/0060687 A1 | 2/2020 | Hernández et al. |
| 2020/0078173 A1 | 3/2020 | McNiven et al. |
| 2020/0113678 A1 | 4/2020 | McCann et al. |
| 2020/0121460 A1 | 4/2020 | Dale et al. |
| 2020/0121894 A1 | 4/2020 | Prabhu et al. |
| 2020/0187942 A1 | 6/2020 | Wei |
| 2020/0205829 A1 | 7/2020 | Wei |
| 2020/0245998 A1 | 8/2020 | Basude et al. |
| 2020/0261107 A1 | 8/2020 | Cohen |
| 2020/0281591 A1 | 9/2020 | Krone et al. |
| 2020/0323528 A1 | 10/2020 | Khairkhahan |
| 2020/0323549 A1 | 10/2020 | Goldfarb et al. |
| 2020/0323634 A1 | 10/2020 | Von Oepen et al. |
| 2020/0360018 A1 | 11/2020 | Dell et al. |
| 2020/0367871 A1 | 11/2020 | Van Hoven et al. |

FOREIGN PATENT DOCUMENTS

| | | |
|---|---|---|
| EP | 0 558 031 B1 | 9/1993 |
| EP | 1 383 448 B1 | 6/2008 |
| EP | 3 649 963 A2 | 5/2020 |
| FR | 2 768 324 A1 | 3/1999 |
| FR | 2 768 325 B1 | 11/1999 |
| WO | WO 91/01689 A1 | 2/1991 |
| WO | WO 91/15155 A1 | 10/1991 |
| WO | WO 92/12690 A1 | 8/1992 |
| WO | WO 94/018893 A1 | 9/1994 |
| WO | WO 96/32882 A1 | 10/1996 |
| WO | WO 97/27807 A1 | 8/1997 |
| WO | WO 98/07375 A1 | 2/1998 |
| WO | WO 99/07354 A2 | 2/1999 |
| WO | WO 99/13777 A1 | 3/1999 |
| WO | WO 99/15223 A1 | 4/1999 |
| WO | WO 00/03759 A2 | 1/2000 |
| WO | WO 00/60995 A2 | 10/2000 |
| WO | WO 01/28432 A1 | 4/2001 |
| WO | WO 03/020179 A1 | 3/2003 |
| WO | WO 03/049619 A2 | 6/2003 |
| WO | WO 2004/069055 A2 | 8/2004 |
| WO | WO 2004/069055 A3 | 8/2004 |
| WO | WO 2005/035043 A2 | 4/2005 |
| WO | WO 2014/018907 A1 | 1/2014 |
| WO | WO 2014/182849 A1 | 11/2014 |
| WO | WO 2015/057289 A1 | 4/2015 |
| WO | WO 2016/178722 A1 | 11/2016 |
| WO | WO 2018/093663 A1 | 5/2018 |

OTHER PUBLICATIONS

International Search Report and Written Opinion dated Sep. 17, 2020 in International Application No. PCT/US2020/034291.

International Search Report dated Jan. 29, 2018 in International Application No. PCT/US2017/062734, European Patent Office, pp. 1-4.

International Search Report dated Jul. 18, 2013 in International Application No. PCT/US2013/038073.

International Search Report dated Jun. 12, 2018 in International Application No. PCT/US2018/019033.

International Search Report dated Oct. 13, 2017 from International Application No. PCT/US2017/039811, European Patent Office ISA/EP.

Vismara et al., Transcatheter Edge-to-Edge Treatment of Functional Tricuspid. Regurgitation in an Ex Vivo Pulsatile Heart Model, JACC 68(10):1024-1033 (2016).

Extended European Search Report dated Mar. 1, 2022 in Application No. EP 21201070.

* cited by examiner

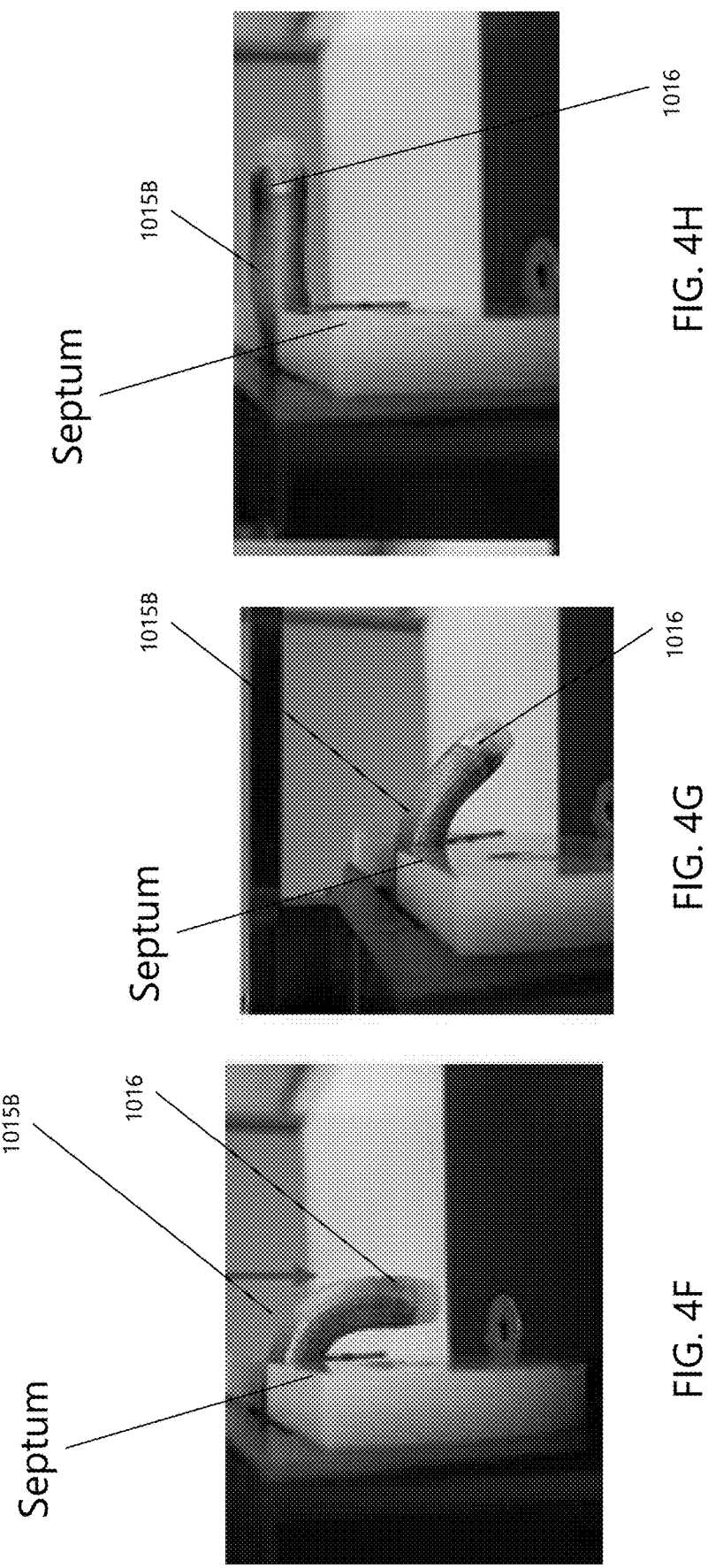

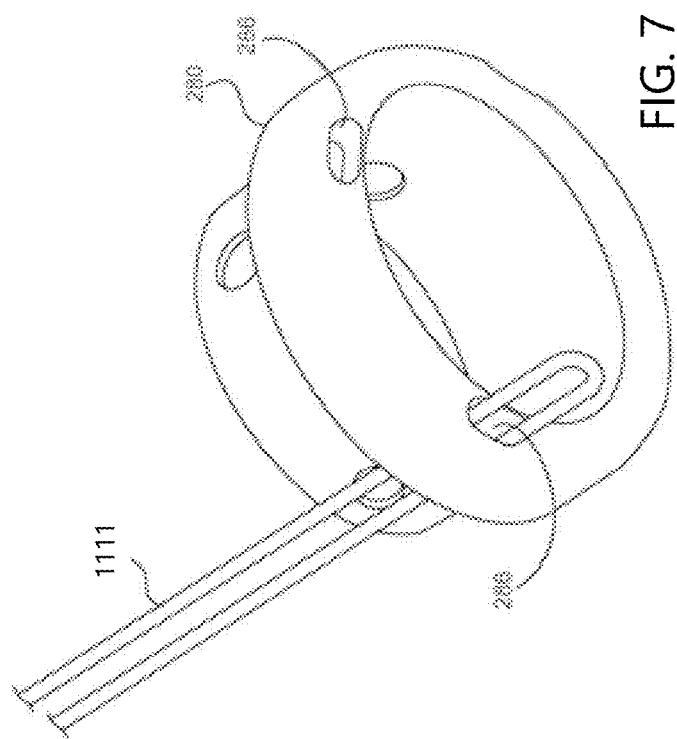

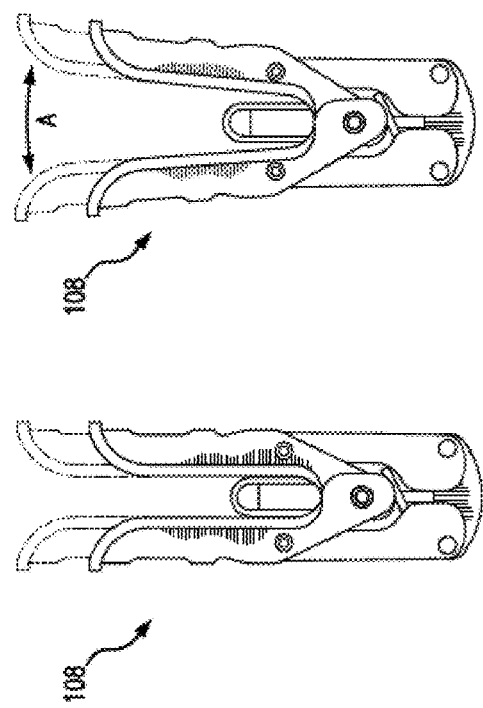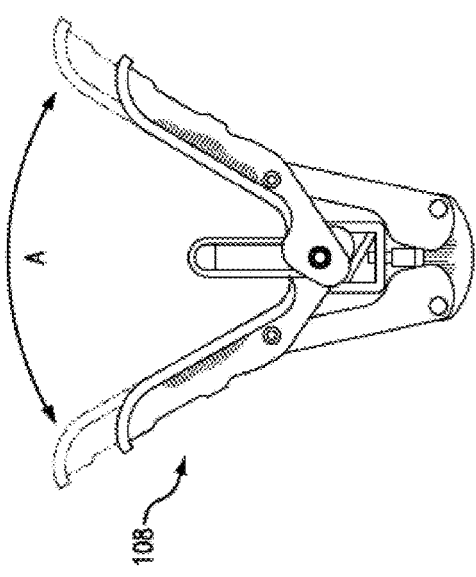
FIG. 13A
FIG. 13B
FIG. 13C

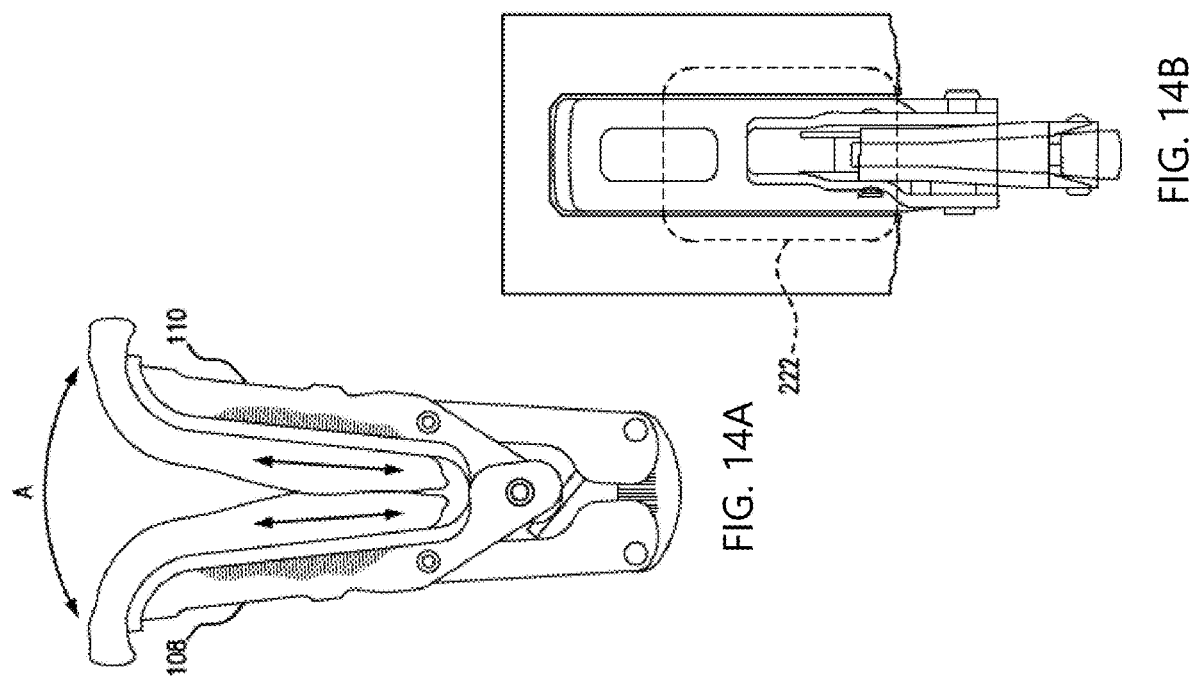

DEVICES AND SYSTEMS FOR ACCESSING AND REPAIRING A HEART VALVE

CROSS-REFERENCE TO RELATED APPLICATIONS

The present application claims the benefit of U.S. Provisional Patent Application No. 63/007,854, filed on Apr. 9, 2020, the full disclosures of which are hereby incorporated herein by reference.

BACKGROUND

Field of Disclosed Subject Matter

The disclosed subject matter is directed to medical devices for endovascular, percutaneous or minimally invasive surgical treatment of bodily tissues, such as tissue approximation or valve repair. More particularly, the present disclosure relates to repair of valves of the heart, such as the tricuspid valve, and venous valves.

The tricuspid valve regulates blood flow in the heart between the right atrium and the right ventricle. A properly functioning tricuspid valve opens and closes to enable blood flow in one direction—i.e., from the right atrium to the right ventricle. When the right ventricle contracts, the tricuspid valve closes to prevent blood from flowing backwards from the right ventricle to the right atrium, and blood is instead forced through the pulmonary valve and into the pulmonary arteries for delivery to the lungs. However, in some circumstances the tricuspid valve is unable to close properly, allowing blood to regurgitate back into the atrium. Such regurgitation can result in shortness of breath, fatigue, heart arrhythmias, and even heart failure.

Tricuspid valve regurgitation has several causes. Functional tricuspid valve regurgitation (FTR) is characterized by structurally normal tricuspid valve leaflets that are nevertheless unable to properly coapt with one another to close properly due to other structural deformations of surrounding heart structures. For example, the right ventricle can become dilated as a result of pulmonary hypertension or an abnormal heart muscle condition (cardiomyopathy).

Other causes of tricuspid valve regurgitation are related to degenerative valves and/or defects of the tricuspid valve leaflets, tricuspid valve annulus, or other tricuspid valve structures. In some circumstances, tricuspid valve regurgitation is a result of infective endocarditis, blunt chest trauma, rheumatic fever, Marfan syndrome, carcinoid syndrome, improper placement of pacemaker leads, or congenital defects to the structure of the heart.

Tricuspid valve conditions are also often associated with problems related to the left side of the heart, such as mitral valve regurgitation. In particular, FTR is often associated with left heart pathologies, though the tricuspid valve is typically left untreated during left heart surgeries. Left heart pathologies such as mitral valve regurgitation and stenosis can induce pressure and volume overload in the right ventricle, which in turn can induce ventricle enlargement and tricuspid annular dilation. Though often relatively mild at the time of treatment of the left heart, this annular dilation of the tricuspid valve can be progressive and asymmetric, and FTR can become more severe as time goes on. Reoperation for repair of the tricuspid valve is often needed owing to the degenerative character of the pathology.

DESCRIPTION OF RELATED ART

Tricuspid valve regurgitation is often treated by replacing the tricuspid valve with a replacement valve implant. However, some patients are not suitable candidates for a valve replacement procedure.

Other treatment options involve repairing the valve through an interventional procedure. Surgical repair of bodily tissues can involve tissue approximation and fastening of such tissues in the approximated arrangement. When repairing valves, tissue approximation (also referred to as "edge-to-edge" repair technique) includes coapting the leaflets of the valve in a therapeutic arrangement which can then be maintained by fastening or fixing the leaflets. Preferably, devices and systems for tricuspid valve repair can be utilized without open chest access, and, rather, can be capable of being performed endovascularly, i.e., delivering repair devices (e.g., a fixation device, also referred to as a valve repair clip) using delivery systems advanced to the heart from a point in the patient's vasculature remote from the heart.

However, properly positioning and aligning a repair device with respect to the tricuspid valve can be difficult, particularly when approaching the tricuspid valve via the inferior vena cava. FIG. 1A illustrates a schematic cut-away, top-down view of the heart, including the location of the four heat valves (tricuspid, mitral, aortic, and pulmonary) as well as the approximate location of the inferior vena cava. The tricuspid valve typically includes three leaflets: posterior leaflet, anterior leaflet, and septal leaflet. When approaching the mitral valve via inferior vena cava, a delivery system will approach through (up through the page) the inferior vena cava, across the right atrium above the tricuspid valve, across the septum and into the left atrium, and back toward (down into the page) the mitral valve. When approaching the tricuspid valve via the inferior vena cava, a delivery system will approach through (up through the page) the inferior vena cava, then immediately back toward (down into the page) the tricuspid valve, all within the right atrium. This can make maneuverability of the distal end of the delivery system more challenging. As an example, the distal end portion of the delivery system must be steered across a severe angle within the right atrium without engaging the right atrium wall or interfering with the tricuspid valve prior to aligning and deploying the repair device. Accordingly, there is a need for devices and systems capable of accessing the tricuspid valve via the inferior vena cava. Such devices and systems likewise can be useful for repair of other heart valves and tissues in the body other than heart valves.

SUMMARY

The purpose and advantages of the disclosed subject matter will be set forth in and apparent from the description that follows, as well as will be learned by practice of the disclosed subject matter. Additional advantages of the disclosed subject matter will be realized and attained by the systems and methods particularly pointed out in the written description and claims hereof, as well as from the appended drawings.

To achieve these and other advantages and in accordance with the purpose of the disclosed subject matter, as embodied and broadly described, the disclosed subject matter is directed to systems and methods for repairing a tricuspid valve.

In accordance with the disclosed subject matter, a medical delivery system for accessing a tricuspid valve via an inferior vena cava is provided. The system includes an outer guide catheter, an inner guide catheter, and an interventional catheter. The outer guide catheter includes a proximal end portion, a first deflection portion, a second deflection portion, and a distal end portion each aligned in series along a length of the outer guide catheter. The outer guide catheter also includes a steering assembly comprising a first steering mechanism and a second steering mechanism. The outer guide catheter defines a lumen extending from the proximal end portion to the distal end portion. The inner guide catheter is position coaxially within the lumen of the outer guide catheter, and includes a proximal end portion, a first deflection portion, and a distal end portion each aligned in series along a length of the inner guide catheter. The inner guide catheter also includes a steering assembly consisting essentially of a first steering mechanism. The inner guide catheter defines a lumen extending from the proximal end portion to the distal end portion. The interventional catheter is positioned coaxially within the lumen of the inner guide catheter. The interventional catheter includes a proximal end portion and a distal end portion, and an implantable fixation device coupled to the distal end portion. The first deflection portion of the outer guide catheter is steerable to define a first outer-guide-catheter curve and the second deflection portion of the outer guide catheter is steerable to define a second outer-guide-catheter curve. The first deflection portion of the inner guide catheter is steerable to define a first inner-guide-catheter curve.

In accordance with the disclosed subject matter, the first steering mechanism of the outer guide catheter can be configured to steer the first deflection portion of the outer guide catheter, and the second steering mechanism of the outer guide catheter can be configured to steer the second deflection portion of the outer guide catheter. At least one of the first outer-guide-catheter curve and the second outer-guide-catheter curve can be preformed in the outer guide catheter. For example, the second outer-guide-catheter curve can be preformed in the outer guide catheter. Both the first outer-guide-catheter curve and the second outer-guide-catheter curve can be preformed in the outer guide catheter.

The first steering mechanism of the inner guide catheter can be configured to steer the first deflection portion of the inner guide catheter. The first inner-guide-catheter curve can be preformed in the inner guide catheter. The second outer-guide-catheter curve can be in a first plane and the first inner-guide-catheter curve can be in a second plane. The first plane and the second plane can be the same plane.

The implantable fixation device can include a first arm and a second arm, a first proximal element moveable relative the first arm between a first position and a second position, and a second proximal element moveable relative to the second arm between a first position and a second position.

In accordance with the disclosed subject matter, a method of repairing a tricuspid valve is provided. The method can include providing a medical delivery system for accessing the tricuspid valve. The medical delivery system can include an outer guide catheter, and inner guide catheter, and an interventional catheter. The outer guide catheter can have a proximal end portion, a first deflection portion, a second deflection portion, and a distal end portion each aligned in series along a length of the outer guide catheter, and a steering assembly including a first steering mechanism and a second steering mechanism. The outer guide catheter can define a lumen extending from the proximal end portion to the distal end portion. The inner guide catheter can be positioned coaxially within the lumen of the outer guide catheter. The inner guide catheter can include a proximal end portion, a first deflection portion, and a distal end portion each aligned in series along a length of the inner guide catheter, and a steering assembly consisting essentially of a first steering mechanism. The inner guide catheter can define a lumen extending from the proximal end portion to the distal end portion. The interventional catheter can be positioned coaxially within the lumen of the inner guide catheter. The interventional catheter can include a proximal end portion and a distal end portion, and have an implantable fixation device coupled to the distal end portion. The method can include delivering the outer guide catheter to a right atrium via an inferior vena cava. The method can further include actuating the first steering mechanism of the outer guide catheter to steer the first deflection portion of the outer guide catheter such that the distal end portion of the outer guide catheter moves within the right atrium relative the tricuspid valve and advancing the inner guide catheter longitudinally relative the outer guide catheter such that the first deflection portion of the inner guide catheter extends distally from the distal end portion of the outer guide catheter. The method can include actuating the first steering mechanism of the inner guide catheter to steer the first deflection portion of the inner guide catheter such that the distal end portion of the inner guide catheter moves within the right atrium relative the tricuspid valve and aligning the implantable fixation device with the tricuspid valve by operating the first and second steering mechanism of the outer guide catheter and the first steering mechanism of the inner guide catheter. The method can include deploying the implantable fixation device to repair the tricuspid valve.

The first deflection portion of the outer guide catheter can be steerable to define a first outer-guide-catheter curve and the second deflection portion of the outer guide catheter can be steerable to define a second outer-guide-catheter curve. The first deflection portion of the inner guide catheter can be steerable to define a first inner-guide-catheter curve. The first outer-guide-catheter curve can be in a first plane and the first inner-guide-catheter curve can be in a second plane. The first plane and the second plane can be the same plane.

The implantable fixation device can include a first arm and a second arm, a first proximal element moveable relative the first arm between a first position and a second position, and a second proximal element moveable relative to the second arm between a first position and a second position.

BRIEF DESCRIPTION OF THE FIGURES

FIGS. 4F-4H are sequential side views of an exemplary delivery system with a portion of an exemplary medical delivery system being steered along a second deflection portion of the outer guide catheter.

FIG. 7 is a perspective view of an exemplary tip ring in accordance with the disclosed subject matter.

FIGS. 13A-13C are front views of the fixation device of FIG. 11 at various positions, wherein optional arms of greater length are depicted with dashed lines.

FIG. 14A is a front schematic view of the fixation device of FIG. 11 having leaflets captured therein.

FIG. 14B is a side view of the fixation device of FIG. 11 schematically depicting a contact patch area.

DETAILED DESCRIPTION

Figure 1:
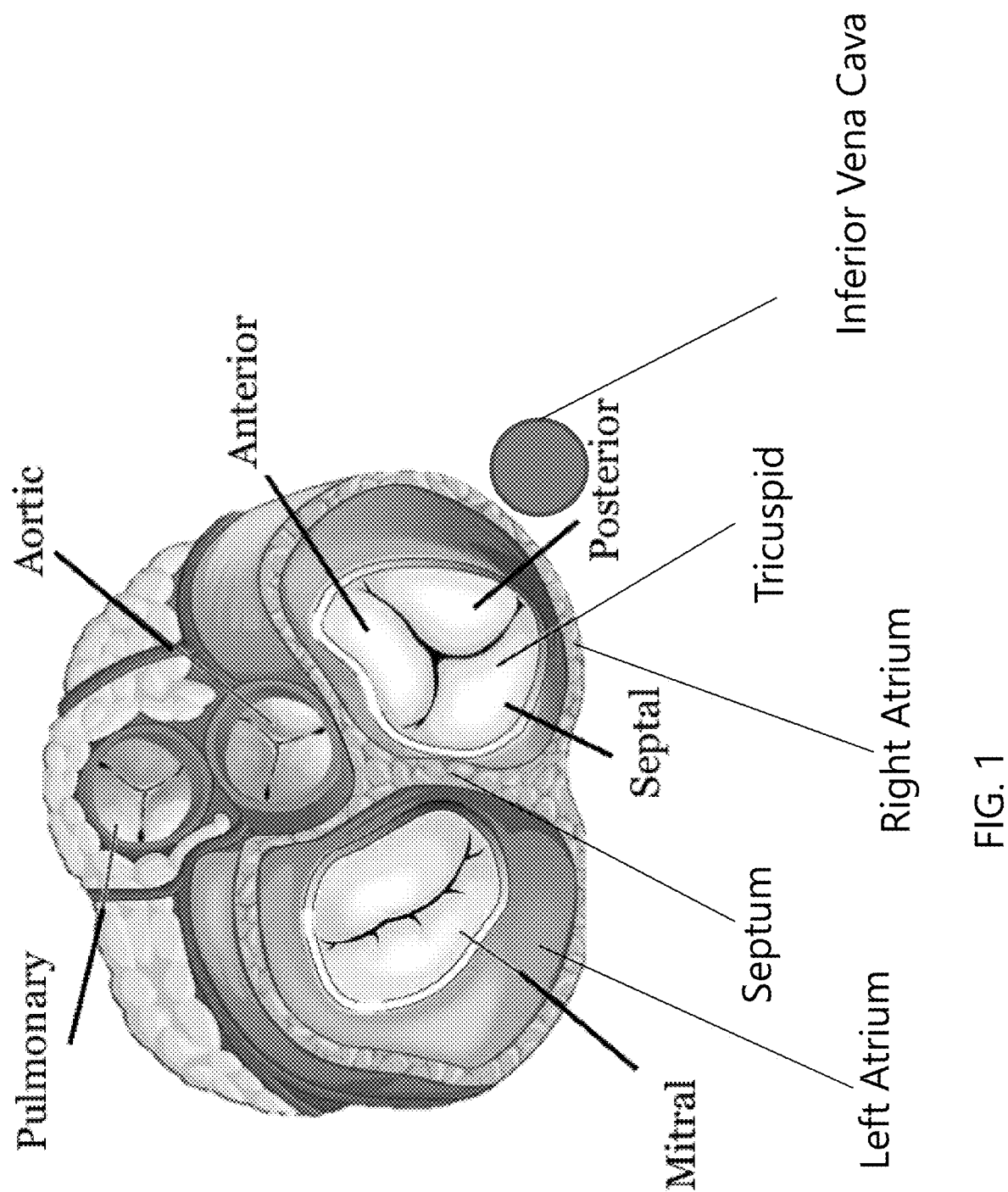
FIG. 1 is a schematic top down, cut-away view of the heart showing the left and right atriums and the four heart valves.

Reference will now be made in detail to the various exemplary embodiments of the disclosed subject matter, exemplary embodiments of which are illustrated in the accompanying drawings.

Transcatheter (e.g., trans-septal) edge-to-edge valve repair for the mitral valve has been established using a fixation device, such as the MitraClip Transcatheter Mitral Valve Repair device. These fixation devices generally are configured to capture and secure opposing native leaflets using two types of leaflet contacting elements. The first element is a sub-valvular arm (also known as a distal element or fixation element) to contact the ventricular side of a native leaflet to be grasped. With the arm positioned underneath to stabilize the native leaflet in a beating heart, a second gripping element (also known as a proximal element) can be lowered or moved into contact with the atrial side of the native leaflet to capture the leaflet therebetween. Once each opposing leaflet is captured by a respective arm and gripper element, the fixation device can be closed by moving the arms toward a center of the fixation device such that the leaflets are brought into coaptation, which results in a reduction in valvular regurgitation during ventricular systole. Furthermore, a covering can be provided on the arms and/or gripper elements to facilitate tissue ingrowth with the captured leaflets. Such fixation devices can be delivered to the mitral valve using a delivery system. There is also evidence that the MitraClip device can be useful in tricuspid valve repair.

Additional details of exemplary fixation devices and delivery systems in accordance with the disclosed subject matter are set forth below. Furthermore, various patents and published applications disclose additional details of such fixation devices and delivery systems and related operations, for example, U.S. Pat. No. 7,226,467 to Lucatero et al., U.S. Pat. No. 7,563,267 to Goldfarb et al., U.S. Pat. No. 7,655,015 to Goldfarb et al., U.S. Pat. No. 7,736,388 to Goldfarb et al., U.S. Pat. No. 7,811,296 to Goldfarb et al., U.S. Pat. No. 8,057,493 to Goldfarb et al., U.S. Pat. No. 8,303,608 to Goldfarb et al., U.S. Pat. No. 8,500,761 to Goldfarb et al., U.S. Pat. No. 8,734,505 to Goldfarb et al., U.S. Pat. No. 8,740,920 to Goldfarb et al., U.S. Pat. No. 9,510,829 to Goldfarb et al., U.S. Pat. No. 7,635,329 to Goldfarb et al., U.S. Pat. No. 8,945,177 to Dell et al., U.S. Pat. No. 9,011,468 to Ketai et al., U.S. Patent Application Publication No. 2017/0042546 to Goldfarb et al., U.S. Patent Application Publication No. 2018/0146966 to Hernandez et al., U.S. Patent Application Publication No. 2017/0239048 to Goldfarb et al., U.S. Patent Application Publication No. 2018/0325671 to Abunassar et al., the entirety of the contents of each of these patents and published applications is incorporated herein by reference.

In accordance with the disclosed subject matter, a medical delivery system for accessing a tricuspid valve via an inferior vena cava is provided. The system includes an outer guide catheter, an inner guide catheter, and an interventional catheter. The outer guide catheter includes a proximal end portion, a first deflection portion, a second deflection portion, and a distal end portion each aligned in series along a length of the outer guide catheter. The outer guide catheter also includes a steering assembly comprising a first steering mechanism and a second steering mechanism. The outer guide catheter defines a lumen extending from the proximal end portion to the distal end portion. The inner guide catheter is position coaxially within the lumen of the outer guide catheter, and includes a proximal end portion, a first deflection portion, and a distal end portion each aligned in series along a length of the inner guide catheter. The inner guide catheter also includes a steering assembly consisting essentially of a first steering mechanism. The inner guide catheter defines a lumen extending from the proximal end portion to the distal end portion. The interventional catheter is positioned coaxially within the lumen of the inner guide catheter. The interventional catheter includes a proximal end portion and a distal end portion, and an implantable fixation device coupled to the distal end portion. The first deflection portion of the outer guide catheter is steerable to define a first outer-guide-catheter curve and the second deflection portion of the outer guide catheter is steerable to define a second outer-guide-catheter curve. The first deflection portion of the inner guide catheter is steerable to define a first inner-guide-catheter curve.

Figure 2:
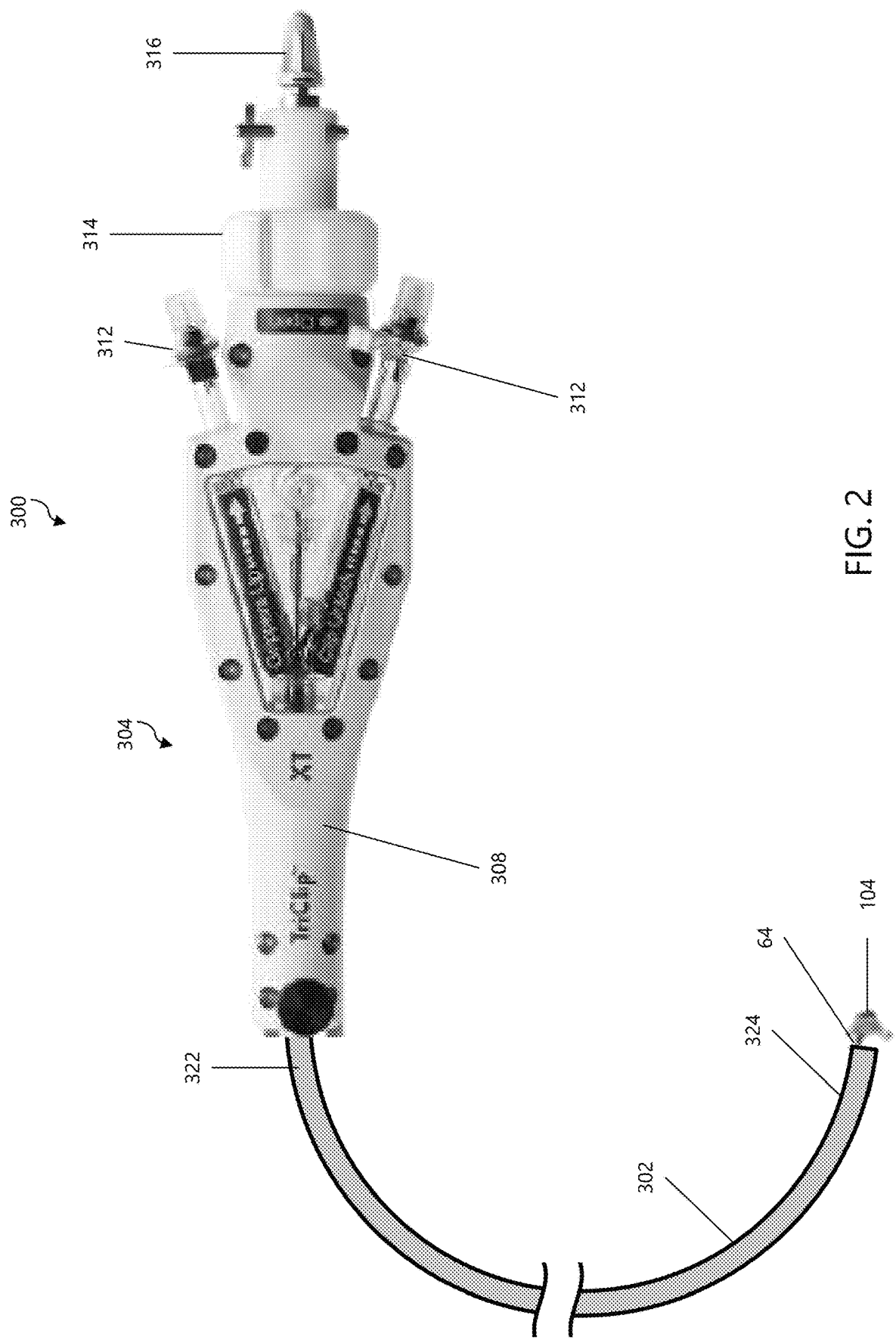
FIG. 2 is a perspective view of an exemplary interventional catheter assembly in accordance with the disclosed subject matter.

Referring to FIG. 2 for purpose of illustration and not limitation, an exemplary interventional catheter assembly 300 is provided for delivery of a fixation device, such as fixation device 104 (described in greater detail below). That is, the interventional catheter assembly 300 can be used to introduce and position a fixation device 104. The interventional catheter assembly 300 can include an interventional catheter 302, having a proximal end portion 322 and a distal end portion 324, and a handle 304 attached to the proximal end portion 322. A fixation device 104 can be removably coupleable to the distal end portion 324 for delivery to a site within the body, for example, the tricuspid valve. Thus, extending from the distal end portion 324 is actuator rod 64. The actuator rod 64 is connectable with the fixation device 104 and can act to manipulate the fixation device 104, for example, opening and closing the arms. Handle 304 of the interventional catheter assembly 300 is shown, including main body 308, proximal element line handle 312, lock line handle 310, the actuator rod control 314, and the actuator rod handle 316, among other features.

Figure 3A:
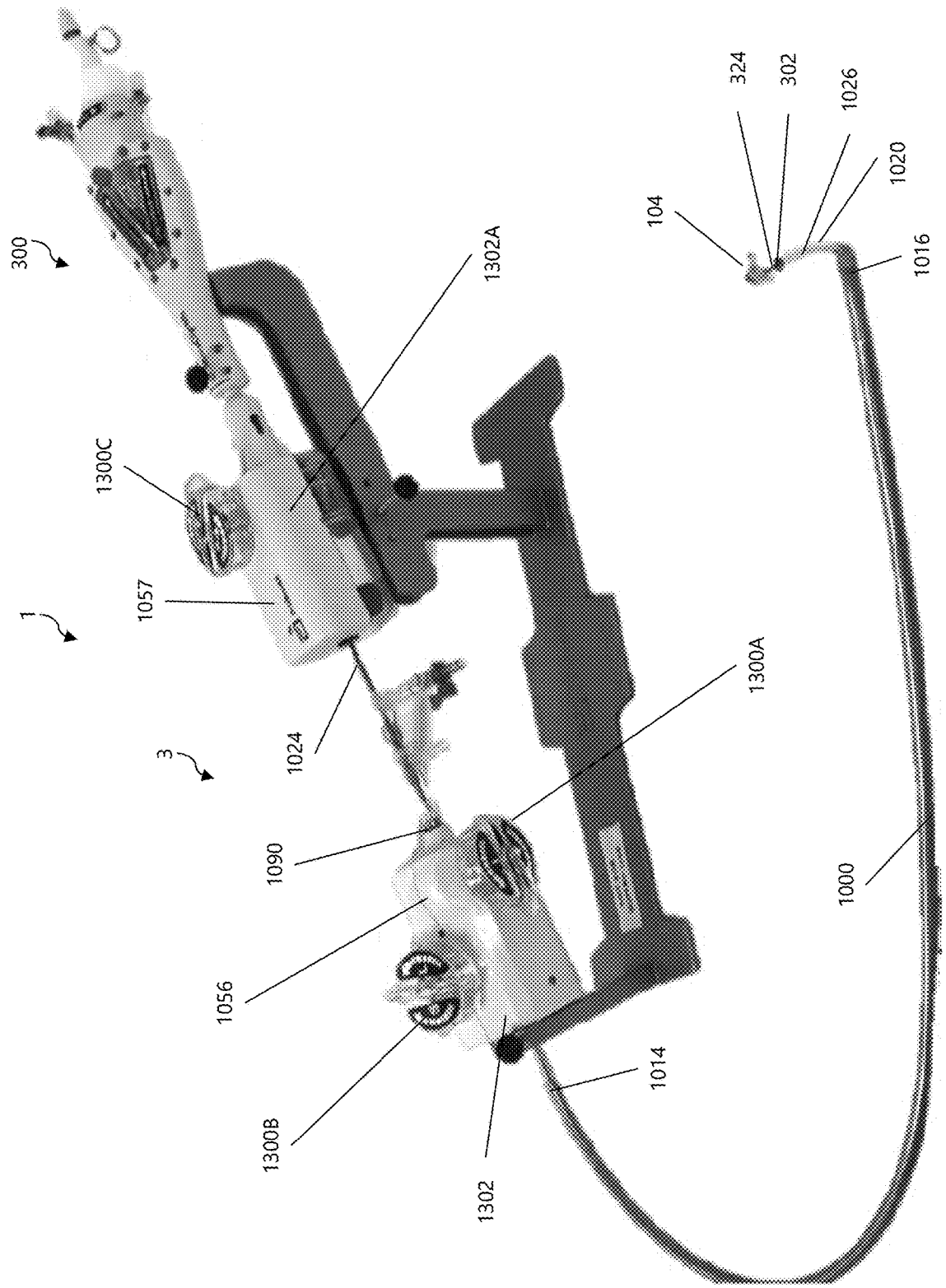
FIG. 3A is a perspective view of an exemplary medical delivery system for accessing and repairing a heart valve, in accordance with the disclosed subject matter.
Figure 3B:
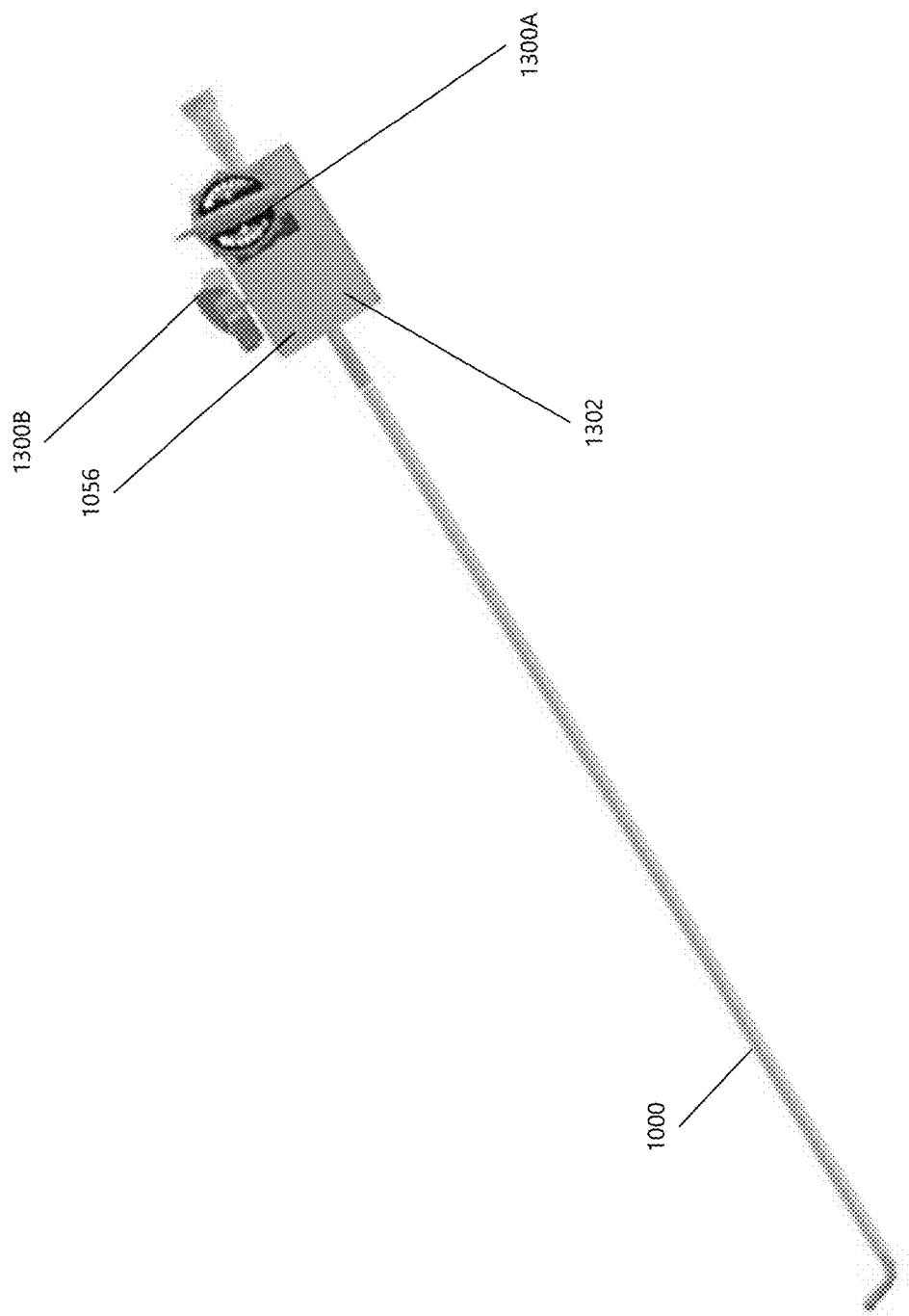
FIG. 3B is a perspective view of an exemplary outer guide catheter and handle in accordance with the disclosed subject matter.
Figure 3C:
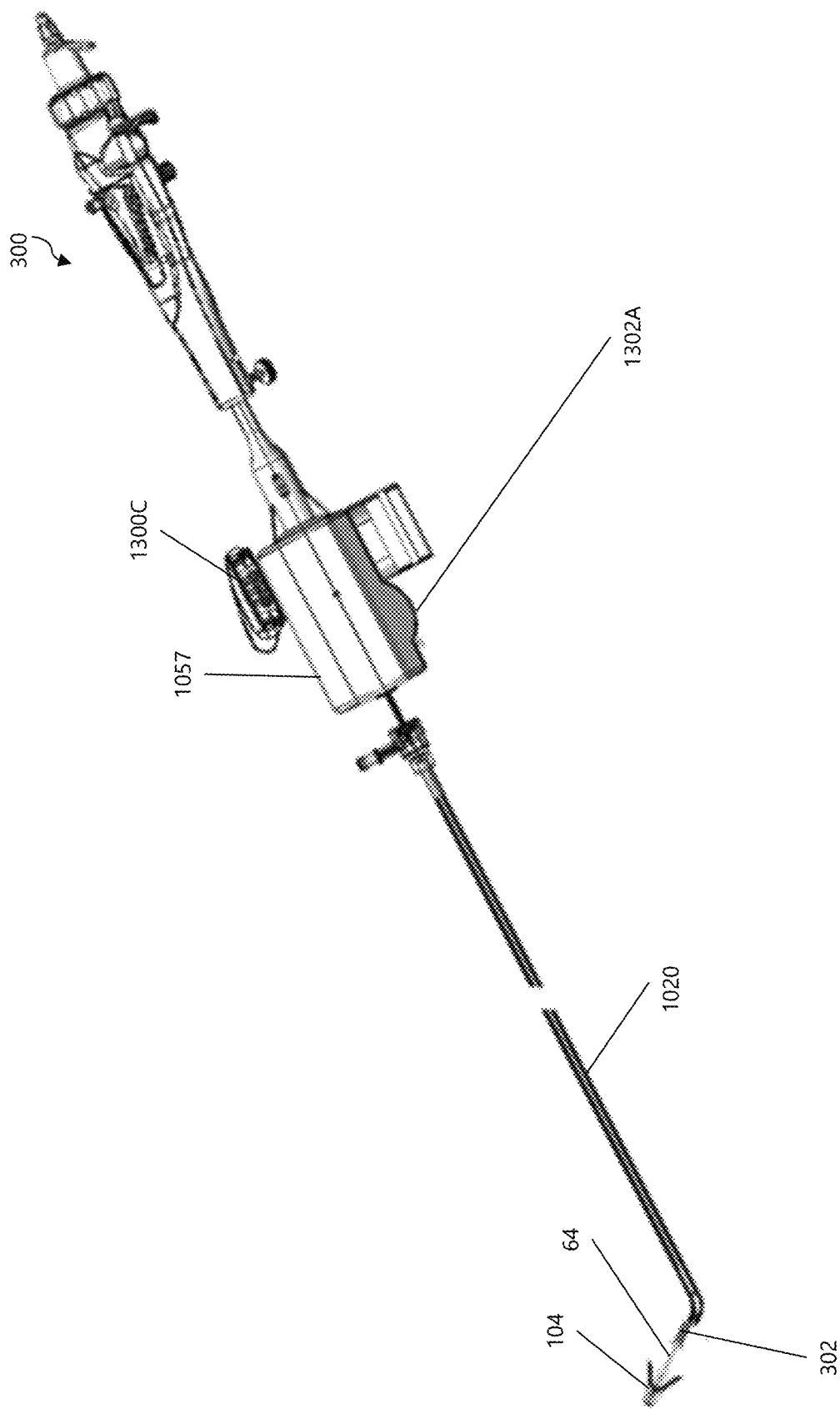
FIG. 3C is a perspective view of an exemplary clip delivery system in accordance with the disclosed subject matter.

Referring to FIGS. 3A-3C for purpose of illustration and not limitation, medical delivery system 1 including an outer guide catheter 1000 and an inner guide catheter 1020 (e.g., collectively steerable guide system 3) and interventional catheter assembly 300 is provided. In accordance with the disclosed subject matter, the inner guide catheter 1020 can also be referred to as a sleeve. FIG. 3B shows, for purpose of illustration and not limitation, the outer guide catheter 1000 and handle 1056, which can collectively be referred as the steerable guide catheter. FIG. 3C shows, for purpose of illustration and not limitation, the interventional catheter assembly 300, the inner guide catheter 1020, and handle 1057, which can collectively be referred to as the clip delivery system.

The steerable guide system 3 can include one or more steerable catheter components. For example, and not limitation, steerable guide system 3 can include an outer guide catheter 1000, having a proximal end portion 1014 and a distal end portion 1016, and an inner guide catheter 1020, having a proximal end portion 1024 and a distal end portion 1026, wherein the inner guide catheter 1020 is positioned coaxially within the outer guide catheter 1000, as shown. In addition, a hemostatic valve 1090 can be disposed within handle 1056, or external to handle 1056 as shown, to provide leak-free sealing with or without the inner guide catheter 1020 in place. The distal end portions 1016, 1026 of guide catheters 1000, 1020, respectively, are sized to be passable to a body cavity, typically through a body lumen such as a vascular lumen.

Referring to FIGS. 4A-4H for purpose of illustration and not limitation, outer guide catheter 1000 can include a proximal end portion 1014, a first deflection portion 1015A, a second deflection portion 1015B, and a distal end portion 1016 each aligned in series along a length of the outer guide catheter 1000. The first deflection portion 1015A can be steerable to define a first outer-guide catheter curve 1017A. First outer-guide catheter curve 1017A can have a radius of curvature $R_1$. The radius of curvature $R_1$ can be suitable for positioning within the right atrium proximate the tricuspid valve with the outer guide catheter 1000 extending from the vena cava. As such, distal end portion 1016 can be deflected to the appropriate angle by steering the outer guide catheter 1000 at deflection portion 1015A. The second deflection portion 1015B can be steerable to define a second outer-guide catheter curve 1017B. Second outer-guide catheter curve 1017B can have a radius of curvature $R_2$. The radius of curvature $R_2$ can be suitable for positioning within the right atrium proximate the tricuspid valve with the outer guide catheter 1000 extending from the vena cava. As such, distal end portion 1016 can be deflected to the appropriate angle by steering the outer guide catheter 1000 at deflection portion 1015B. First outer-guide catheter curve 1017A and second outer-guide catheter curve 1017B can be in the same plane or in different planes. For example, first outer-guide catheter curve 1017A and second outer-guide catheter curve 1017B can exist on planes that are orthogonal to one another. The proximal end portion 1014, first deflection portion 1015A, second deflection portion 1015B, and distal end portion 1016 can each have a respective length that can be suitable for positioning within the right atrium proximate the tricuspid valve with the outer guide catheter 1000 extending from the vena cava.

Figure 4A:
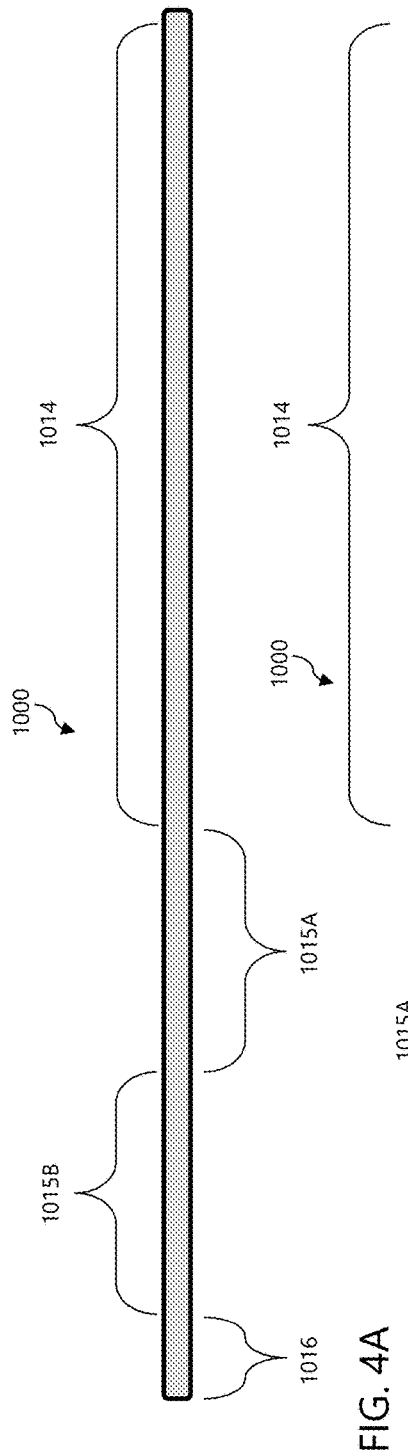
FIGS. 4A-4C are schematic side views of a length of an exemplary outer guide catheter in accordance with the disclosed subject matter.
Figure 4B:
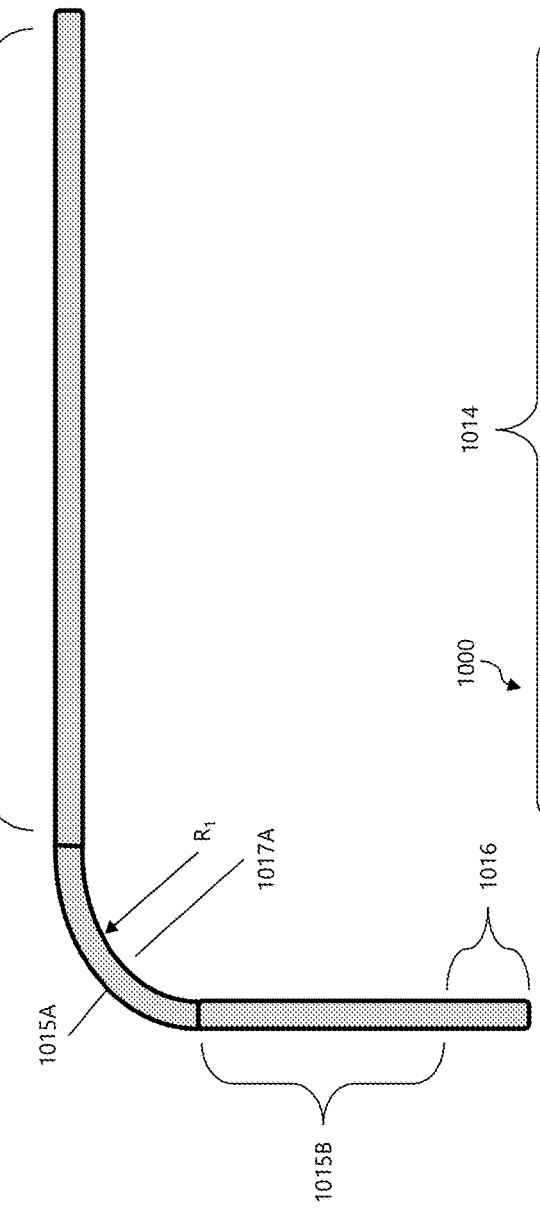
Figure 4C:
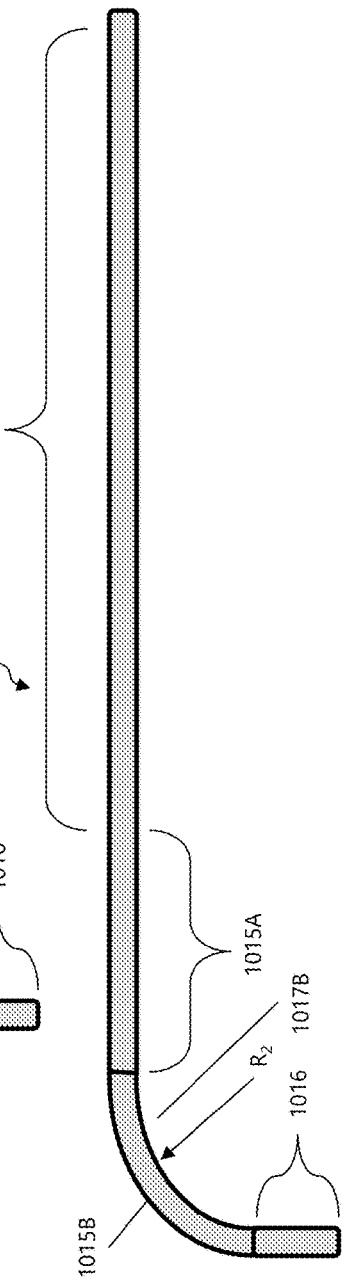
Figure 4E:
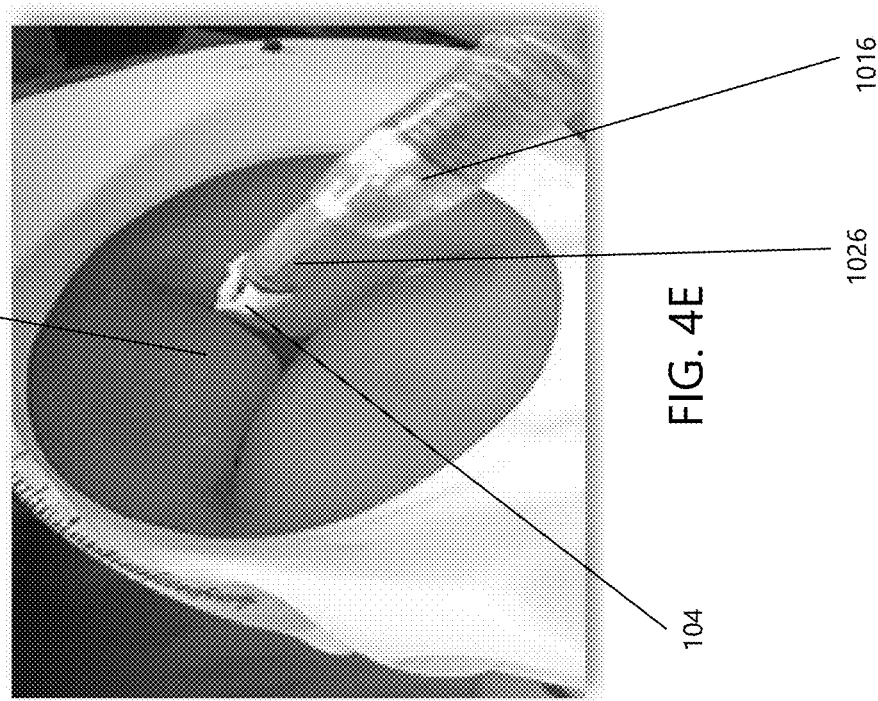
FIGS. 4D-4E are sequential perspective views of a heart valve model with a portion of an exemplary medical delivery system being steered along a first deflection portion of the outer guide catheter.
Figure 4D:
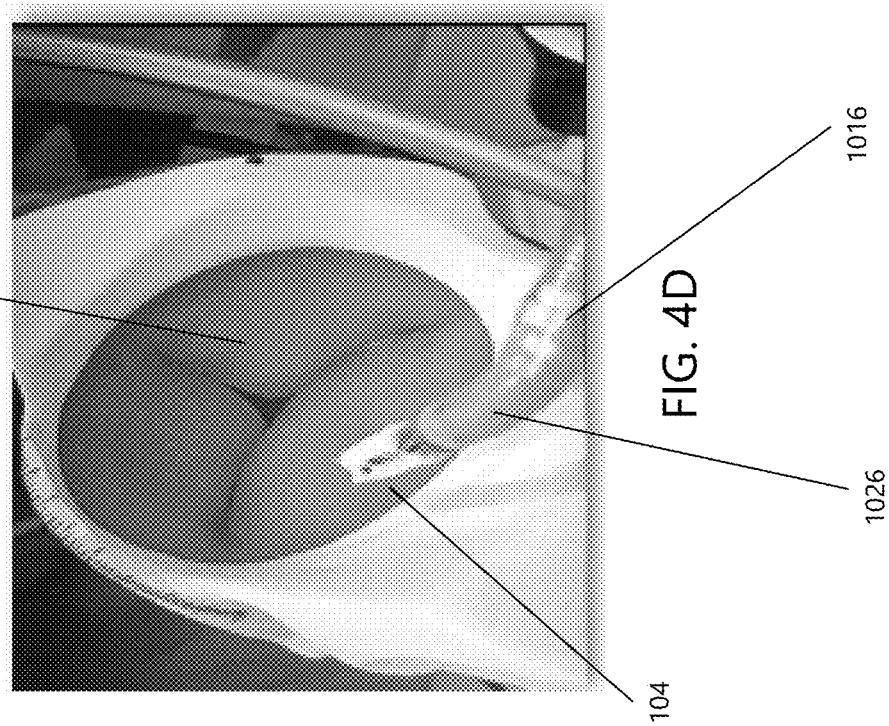

In accordance with the disclosed subject matter, one or more of the proximal end portion 1014, first deflection portion 1015A, second deflection portion 1015B, and distal end portion 1016 can overlap. For example, the proximal end portion 1014 and the first deflection portion 1015A can overlap. First deflection portion 1015A can be a non-preformed deflection portion. For example, as shown in FIGS. 4D-4H and as described in greater detail below, steering the first deflection portion 1015A during use can move the distal end portion 1016 between a septal position (FIG. 4D) and a lateral position (FIG. 4E). For example, steering along first deflection portion 1015A can deflect the distal end portion 1016 about 25 mm. The second deflection portion 1015B can be created by a process of preforming the deflection portion (as described below). For example, the radius of curvature $R_2$ can be about 0.525" (plus/minus about 0.005"), as created by a process of preforming the outer-guide catheter curve 1017A (as described below). The second deflection portion 1015B can include a neutral (or relaxed) state that can include a deflection of the distal end portion 1016 of between 45° and 65°, for example, about 55° (FIG. 4G). As described in greater detail below, outer guide catheter 1000 can be steered during use at the second deflection portion 1015B to move the distal end portion 1016 between positions approximately normal to the proximal end portion 1014 (see FIG. 4F) and approximately linear with the proximal end portion 1014 (see FIG. 4H). The outer guide catheter 1000 can have, for example, an overall length between 98 cm and 102 cm, for example, 100 cm, and a working length between 78 and 82 cm, for example about 80 cm. The proximal end portion 1014 can have a length of between about 74 cm and about 78 cm, for example 76 cm. The distal end portion 1016 and second deflection portion 1015B can have a total length between about 3 cm and 5 cm, for example about 4 cm. The outer guide catheter 1000 can have an outer diameter of about 25 French. It is understood that all dimensions are provided for purpose of illustration and not limitation.

Figure 5A:
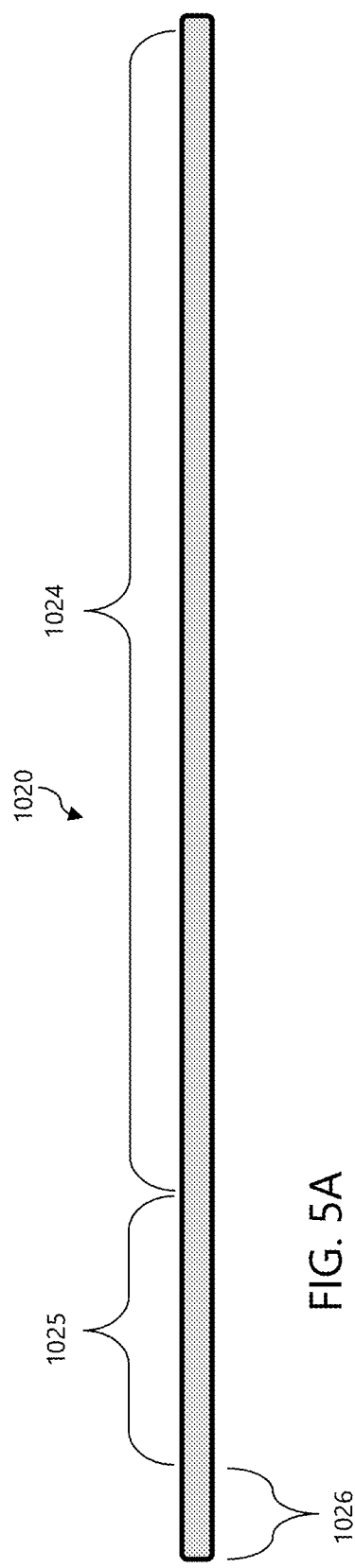
FIGS. 5A-5B are schematic side views of a length of an exemplary inner guide catheter in accordance with the disclosed subject matter.
Figure 5B:
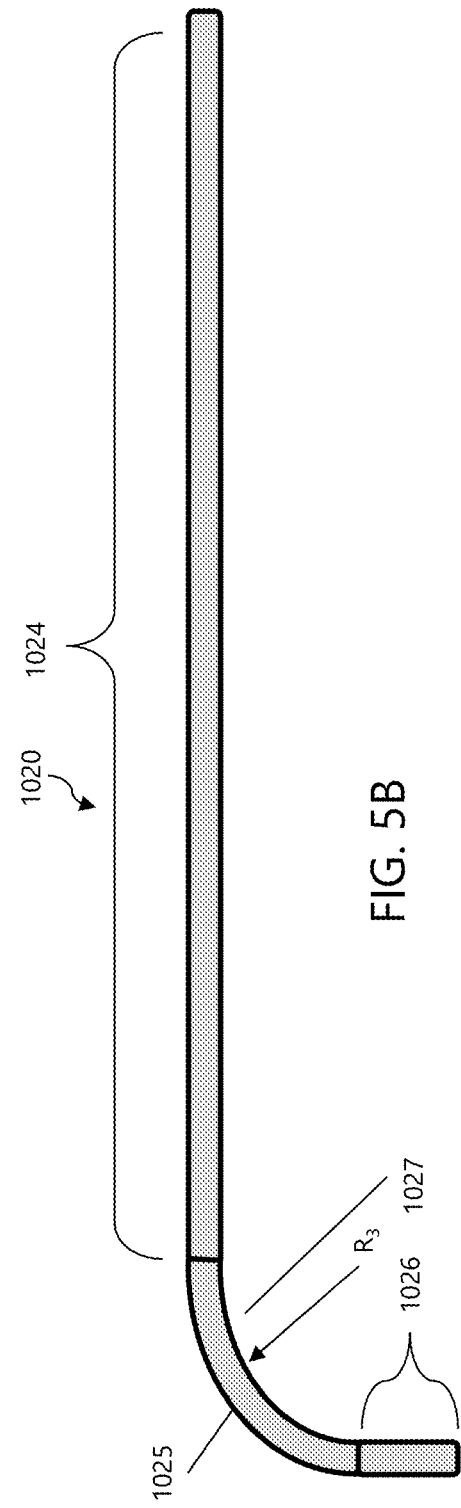

Referring to FIGS. 5A-5B for purpose of illustration and not limitation, inner guide catheter 1020 can include a proximal end portion 1024, deflection portion 1025, and distal end portion 1026 each aligned in series along a length of the outer guide catheter. The deflection portion 1025 can be steerable to define a inner guide-catheter curve 1027. The inner-guide catheter curve 1027 can have a radius of curvature $R_3$. The radius of curvature $R_3$ can be suitable to align with the tricuspid valve when the inner guide catheter 1020 is extending from the outer guide catheter 1000. As such, distal end portion 1026 can be deflected to an appropriate angle by steering the inner guide catheter 1020 at deflection portion 1025. The inner guide-catheter curve 1027 can be in a plane, for example, the same plane as second outer-guide catheter curve 1017B. For example, the inner guide catheter 1020 and the outer guide catheter 1000 can be provided with markers, intended to manually align the two planes, or can be provide with mating or engaging features (such as keying features, as described in greater detail below) to self-align as desired. When the inner-guide catheter curve 1027 and second outer-guide catheter curve 1017B are in the same plane, both guide catheters 1000, 1020 can be adjusted to achieve proper position relative to the tricuspid valve (e.g., alignment relative the valve and height above the valve) such as by compensating for one another, as set forth in greater detail below.

The proximal end portion 1024, deflection portion 1025, and distal end portion 1026 can each have a respective length that can be suitable for positioning within the right atrium proximate the tricuspid valve when the inner guide catheter 1020 is extending from the outer guide catheter 1000. When inner guide catheter 1020 includes one deflection portion (i.e., deflection portion 1025), a limited portion of the inner guide catheter 1020 (e.g., distal end portion 1026 and deflection portion 1025) can extend from the outer guide catheter 1000 to be steered within the right atrium. Adding additional deflection portions can require additional portions of the inner guide catheter 1000 to extend from the outer guide catheter 1000. However, to achieve a more acute delivery angle (for example, the inner guide catheter curve 1027) it can be beneficial to maintain a small profile and omit extraneous catheter features for the inner guide catheter 1020. Therefore, inner guide catheter 1000 can include one deflection portion (i.e., deflection portion 1025).

In accordance with the disclosed subject matter, the deflection portion 1025 can be created by a process of preforming the deflection portion (as described below). For example, and not limitation, the radius of curvature $R_3$ can be about 0.505" (plus/minus about 0.005"), as created by a process of preforming the inner-guide catheter curve 1027 (as described below). The deflection portion 1025 can include a neutral (or relaxed) state that can include a deflection of the distal end portion 1026 of about 45° (plus/minus about 5°). For example, and as described in greater detail below, inner guide catheter 1020 can be steered at the deflection portion 1025 to move the distal end portion 1025 between positions approximately normal to the proximal end portion 1024 (see FIG. 5B) and approximately linear with the proximal end portion 1024 (see FIG. 5A). The inner guide catheter 1020 can have, for example, a length between 107 and 111 cm, for example, about 109.5 cm. The proximal end portion 1024 can have, for example, a length between 100 and 103 cm, for example, about 101.8 cm. The distal end portion 1026 can have a length between 2 cm and 3 cm, for example about 2.5 cm, the deflection portion 1025 can have a length between 4 cm and 7 cm, for example, about 5.5 cm. The inner guide catheter 1020 can have an outer diameter of about 16 French. Again, all dimensions are provided for purpose of illustration and not limitation.

The curvatures can be formed in catheters 1000, 1020 by preforming (also referred to as precurving), steering or any suitable means. For example, one or more deflection portions 1015A, 1015B, 1025 of guide catheters 1000, 1020 can be curved by a combination of precurving and steering. Precurving involves preforming or setting a specific curvature in the catheter prior to usage, such as by heat setting a polymer or by utilizing a shape-memory alloy. Since the catheters are generally flexible, steering can be used to straighten the catheter throughout the deflection portions 1015A, 1015B, 1025. Once the catheter is positioned in the anatomy, the steering can be adjusted and the catheter can be straightened, relax or bias back toward the preformed setting, or curve further along the predefined curve. In accordance with the disclosed subject matter, one or more of the first outer-guide catheter curve 1017A, second outer-guide catheter curve 1017B, and inner-guide catheter curve 1027, can be preformed. As an example, and not by way of limitation, the second outer-guide catheter curve 1017B and inner-guide catheter curve 1027 can be preformed and the first outer-guide catheter curve 1017A can be non-preformed.

Steering assemblies can be used to steer guide catheters 1000, 1020. The steering assemblies can include one or more steering mechanisms, such as cables or pull wires within the wall of the guide catheters 1000, 1020. For example, a steering mechanism can be provided for each curve portion, such that the outer guide catheter 1000 can include a first steering mechanism to steer the first outer-guide catheter curve 1017A and a second steering mechanism to steer the second outer-guide catheter curve 1017B. The inner guide catheter 1020 can include a first steering mechanism to steer the inner-guide catheter curve 1027. To achieve a more acute delivery angle (for example, the inner guide catheter curve 1027) it can be beneficial to maintain a small profile and omit extraneous catheter features for the inner guide catheter 1020. Therefore inner guide catheter 1020 can consist essentially of a single steering mechanism (i.e., the first steering mechanism).

Figure 6A:
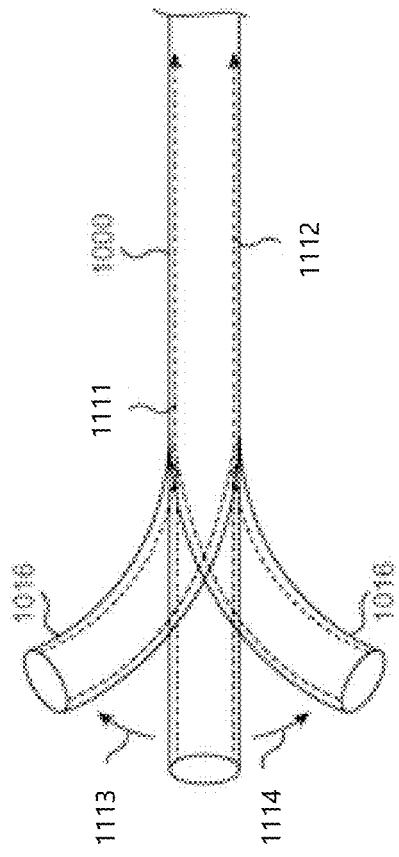
FIGS. 6A-6B are side views of a distal end portion of exemplary catheters including steering mechanisms in accordance with the disclosed subject matter.
Figure 6B:
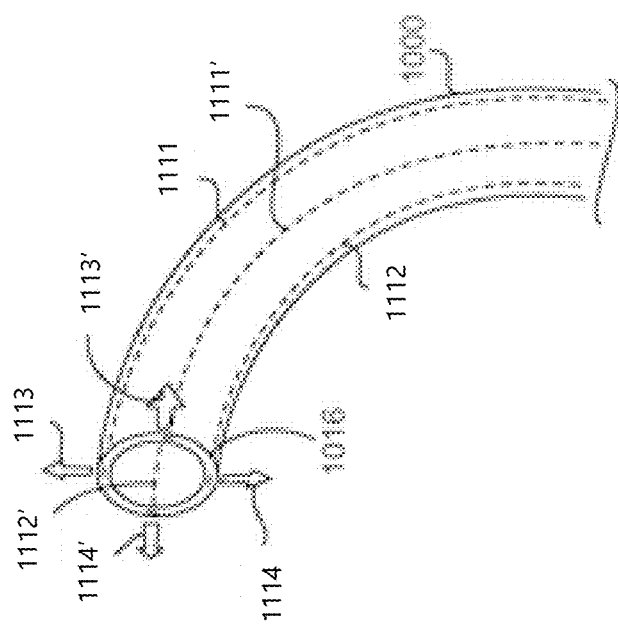

Referring to FIG. 6A for purpose of illustration and not limitation, the outer guide catheter 1000 can include one or more pull wires 1111, 1112 slidably disposed in lumens within the wall of the catheter 1000 and extending to the distal end portion 1016. By applying tension to the pull wire 1111 in the proximal direction, the distal end portion 1016 curves in the direction of the pull wire 1111 as illustrated by arrow 1113. Likewise, by applying tension to pull wire 1112 in the proximal direction, the distal end portion 1016 curves in the direction of pull wire 1112 as illustrated by arrow 1114. Diametrically opposing placement of pull wires 1111, 1112 within the walls of guide catheter 10000 allows the distal end portion 1016 to be steered in opposite directions 1113, 1114. This can provide a means of correcting or adjusting a curvature. For example, if tension is applied to one pull wire to create a curvature, the curvature can be lessened by applying tension to the diametrically opposite pull wire. Referring to FIG. 6B for purpose of illustration and not limitation, an additional set of opposing pull wires 1111' and 1112' can extend within the wall of guide catheter 1000 to steer guide catheter 1000 toward arrows 1113', 1114', respectively. This combination of pull wires 1111, 1112, 1111', 1112' can allow guide catheter 1000 to be curved along first outer-guide catheter curve 1017A and second outer-guide catheter curve 1017B. For example, pull wires 1111, 1112 can be a first steering mechanism and can be used to steer along first outer-guide catheter curve 1017A and pull wires 1111', 1112' can be a second steering mechanism and can be used to steer along second outer-guide catheter curve 1017B. As another example and not by way of limitation, guide catheter 1000 can include two pull wires, for example pull wire 1111 which can be a first steering mechanism and can be used to steer along first outer-guide catheter curve 1017A and pull wire 1111' which can be a second steering mechanism and can be used to steer along second outer-guide catheter curve 1017B. Inner guide catheter 1020, which can be steerable at deflection portion 1025, can include one pull wire 1121 (not shown), which can be a first steering mechanism, or one set of opposing pull wires 1121, 1122 (not shown), which can be a first steering mechanism, to steer along inner guide-catheter curve 1027.

Figure 8:
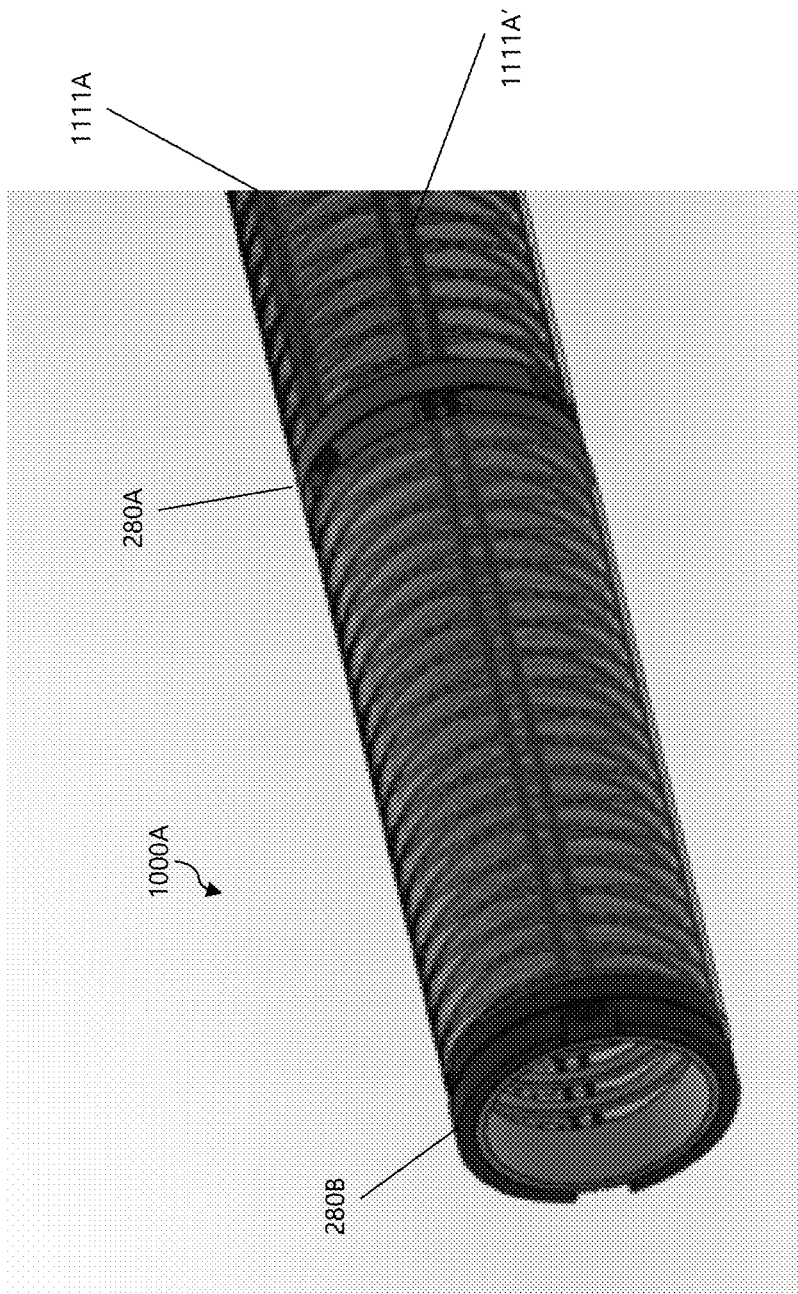
FIG. 8 is a perspective view of a distal end portion of an exemplary catheter including multiple tip rings, in accordance with the disclosed subject matter.

In accordance with the disclosed subject matter, pull wires 1111, 1112, 1111', 1112' and associated lumens can be placed in any arrangement, singly or in pairs, symmetrically or nonsymmetrically, and any number of pull wires can be present. This can allow curvature in any direction and about various axis. The pull wires 1111, 1112, 1111', 1112' can be fixed at any location along the length of the catheter by any suitable method, such as by gluing, tying, soldering, or potting. When tension is applied to the pull wire, the curvature is formed from the point of attachment of the pull wire toward the proximal direction. Therefore, curvatures can be formed throughout the length of the catheter depending upon the locations of the points of attachment of the pull wires (and any precurve formed in the catheter as set forth below). The pull wires can be attached near the distal end of the catheter, the distal end of the first deflection portion 1015A, the distal end of the second deflection portion 1015B, or the distal end of the deflection portion 1025, for example, using tip ring 280, illustrated in FIG. 7. As shown, the pull wire 1111 can pass through an orifice 286 in the tip ring 280, form a loop shape, and pass back through the orifice 286 and travel back through the catheter wall (not shown). The loop formed can be captured by a portion (not shown) of the tip ring 280. For example, a single distal tip ring 280 can be provided in outer guide catheter 1000 and the pull wires 1111, 1112, 1111', 1112' can each be coupled to the distal tip ring 280. In accordance with the disclosed subject matter, catheter 1000 can include two or more tip rings 280 located at different locations along the length of catheter 1000. Referring to FIG. 8 for example, and not by way of limitation, catheter 1000A includes two tip rings 280A, 280B located at different locations along the length of catheter 1000A. Pull wire 1111A passes through an orifice in tip ring 280A, forms a loop shape, and passes back through the orifice to travel back through the catheter wall. Pull wire 1111A' extends through tip ring 280A to tip ring 280B, passes through an orifice in tip ring 280B, forms a loop shape, and passes back through the orifice to travel back through the catheter wall. As noted above, such a configuration can cause the curvature formed by pull wire 1111A to have a different location than the curvature formed by pull wire 1111A'.

Additionally or alternatively, precurvature of the catheter can focus the location of the curvature. For example, when the catheter is precurved at a deflection portion 1015A, 1015B, 1025, the pull wires can be used to straighten the deflection portion 1015A, 1015B, 1025, allow the deflection portion to relax toward the predefined curve, or curve further along the predefined curve. In addition, the lumens which house the pull wires can be straight or curved.

Additionally or alternatively, the delivery approach and native anatomy can focus the location of the curvature. For example, when the catheter is non-precurved at a deflection portion 1015A, 1015B, 1025, the pull wires can be used to steer the guide catheter 1000, 1020, and the native anatomy can focus the steering to the deflection portion 1015A, 1015B, 1025.

The outer guide catheter 1000 and inner guide catheter 1020 can have similar or different construction which can include any suitable material or combination of materials to create the above described curvatures. For example, when one or more deflection portions 1015A, 1015B, 1025 the guide catheter 1000, 1020 is precurved in addition to being steerable, the guide catheter 1000, 1020 can include a polymer or copolymer which is able to be set in a desired curve, such as by heat setting. Likewise, the guide catheter 1000, 1020 can include a shape-memory alloy.

Additionally or alternatively, the guide catheter 1000, 1020 can include one or more of a variety of materials, either along the length of the guide catheter 1000, 1020, or in various segments (e.g., 1014, 1015A, 1015B, 1016). Example materials can include polyurethane, Pebax, nylon, polyester, polyethylene, polyimide, polyethylenetelephtha-late (PET), or polyetheretherketone (PEEK). In addition, the walls of the guide catheter 1000, 1020 can include multiple layers of materials and can be reinforced with a variety of structures, such as metal braids or coils. Such reinforcements can be along the length of the guide catheter 1000, 1020, or in various segments (e.g., 1014, 1015A, 1015B, 1016).

For example, and in accordance with the disclosed subject matter, proximal portions 1014, 1024 can be relatively more rigid and the deflection portions 1015A, 1015B, 1025, and distal portions 1016, 1026 can be relatively less rigid. For example, and not by way of limitation, the proximal portion 1014 can include a nylon extrusion, a stainless steel braid disposed over the nylon extrusion, and a Pebax layer encapsulating the stainless steel braid. The nylon extrusion can include lumens 1404 to receive the pull wires 1111, 1112, 1111', 1112' (see FIG. 9B). The deflection portions 1015A, 1015B and distal portion 1016 can include a Pebax layer. The portions can be fused together using Pebax, and a stainless steel braiding can be placed over the entire catheter 1000. Guide markers can be added over the steel braiding and a layer of Pebax can encapsulate the guide markers and steel braiding. A soft tip can be coupled to the distal portion 1016.

In accordance with the disclosed subject matter, one or more of outer guide catheter 1000, inner guide catheter 1020, and interventional catheter 302 can be combined as a catheter assembly. For example, outer guide catheter 1000 and inner guide catheter 1020 can be combined as a catheter assembly. As another example, inner guide catheter 1020 and interventional catheter 302 can be combined as a catheter assembly. As another example, outer guide catheter 1000, inner guide catheter 1020, and interventional catheter 302 can be combined as a catheter assembly.

Figures 9A, 9B, 9C:
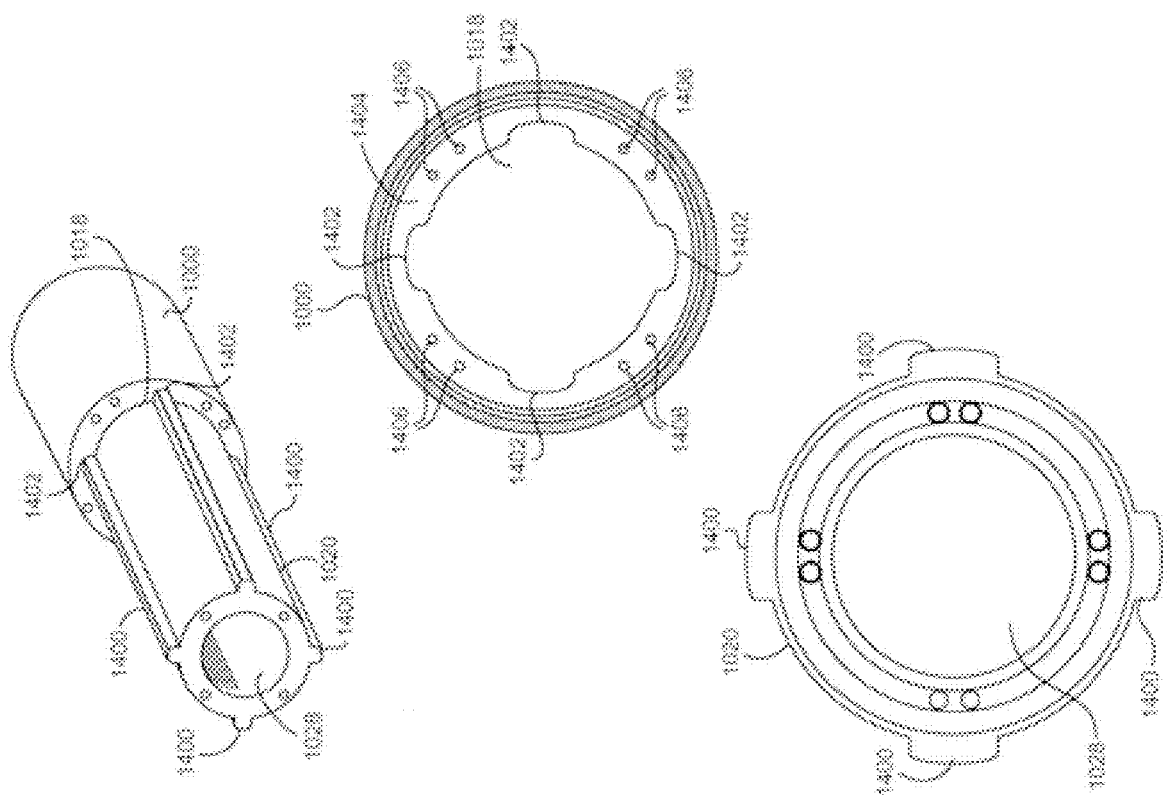
FIG. 9A is a perspective detail view of the engagement between an exemplary outer guide catheter and an exemplary inner guide catheter including notches and protrusions, respectively, in accordance with the disclosed subject matter.
FIG. 9B is a cross-section view of the outer guide catheter of FIG. 9A.
FIG. 9C is a cross-section view of the inner guide catheter of FIG. 9A.

Referring to FIGS. 9A-9C for purpose of illustration and not limitation, outer guide catheter 1000 and inner guide catheter 1020 can include a keying feature. The keying feature can be used to maintain rotational relationship between the guide catheters 1000, 1020 to assist in steering capabilities. For example, inner guide catheter 1020 can include one or more protrusions 1400 which can extend radially outwardly. FIG. 9A illustrates four protrusions 1400, equally spaced around the exterior of the inner guide catheter 1020. Likewise, outer guide catheter 1000 can include corresponding notches 1402, which can align with the protrusions 1400. FIG. 9A illustrates four notches 1402 equally spaced around the central lumen 1018. Thus, inner guide catheter 1020 is able to be translated within outer guide catheter 1000, however rotation of inner guide catheter 1020 is prevented by the keying features, i.e., the interlocking protrusions 1400 and notches 1402. Such keying can help maintain a known correlation of position between the inner guide catheter 1020 and outer guide catheter 1000. Although the protrusions and notches are illustrated on the inner guide catheter 1020, and outer guide catheter 1000, respectively, the protrusions and/or notches can be on either the inner guide catheter 1020 and outer guide catheter 1000, which corresponding protrusions or notches on the other.

FIG. 9B illustrates a cross-sectional view of outer guide catheter 1000 of FIG. 9A. The catheter includes a notched layer 1404 along the inner surface of the central lumen 1018. The notched layer 1404 can include notches 1402 in any size, shape, arrangement and number. Optionally, the notched layer 1404 can include lumens 1406, for passage of pull wires 1111, 1112, 1111', 1112'. However, lumens 1406 can alternatively or additionally have other uses. Notched layer 1404 can be incorporated into the wall of outer guide catheter 1000, such as by extrusion, or can be a separate layer positioned within the outer guide catheter 1000. Notched layer 1404 can extend the entire length of outer guide catheter 1000, the entire length of one or more segments 1014, 1015A, 1015B, 1016, or along a portion of one or more segments 1014, 1015A, 1015B, 1016, including a small strip at a designated location along the length of outer guide catheter 1000.

FIG. 9C illustrates a cross-sectional view of the inner guide catheter 1020 of FIG. 9A. The inner guide catheter 1020 includes protrusions 1400 along the outer surface of the inner guide catheter 1020. The protrusions 1400 can be of any size, shape, arrangement and number. Protrusions can be incorporated into the wall of inner guide catheter 1020, such as by extrusion, or can be included in a separate cylindrical layer on the outer surface of the inner guide catheter 1020. Alternatively, the protrusions 1400 can be individually adhered to the outer surface of guide catheter 1020. Protrusions can extend the entire length of inner guide catheter 1020, the entire length of one or more segments 1024, 1025, 1026, or along a portion of one or more segments 1024, 1025, 1026, including a small strip at a designated location along the length of inner guide catheter 1000.

In accordance with the disclosed subject matter, outer guide catheter 1000 and inner guide catheter 1020 can be provided without keying features.

Referring again to FIGS. 2 and 3 for purpose of illustration and not limitation, manipulation of the guide catheters 1000, 1020 can be achieved with the use of handles 1056, 1057 attached to the proximal end portions 1014, 1024 of catheters 1000, 1020, respectively. As shown, handle 1056 is attached to the proximal end portion 1014 of outer guide catheter 1000 and handle 1057 is attached to the proximal end portion 1024 of inner guide catheter 1020. Inner guide catheter 1020 is inserted through handle 1056 and is positioned coaxially within outer guide catheter 1000. The interventional catheter 302 can be inserted though handle 1057 and can be positioned coaxially within inner guide catheter 1020 and outer guide catheter 1000.

Handle 1056 can include two steering knobs 1300A, 1300B emerging from a handle housing 1302 for manipulation by the user. Steering knob 1300A can be disposed on the side of housing 1302 and steering knob 1300B can be disposed on a face of the housing 1302. Steering knob 1300A can be coupled to pull wires 1111, 1112, which can be arranged to steer the second deflection portion 1015B of outer guide catheter 1000. Steering knob 1300B can be coupled to pull wires 1111', 1112', which can be arranged to steer the first deflection portion 1015A of outer guide catheter 1000. Handle 1057 can include one steering knob 1300C emerging from a handle housing 1302A for manipulation by the user. Steering knob 1300C can be disposed on a face of the housing 1302A. Steering knob 1300C can be coupled to pull wires 1121, 1122, which can be arranged to steer the deflection portion 1025 of inner guide catheter 1020. Although the steering knobs are described in particular locations, placement can be based on a variety of factors, including type of steering mechanism, size and shape of handle, type and arrangement of parts within handle, and ergonomics, among others. Furthermore, while control of the pull wires is illustrated with steering knobs, any control mechanisms can be used, including, for example, sliders, triggers or actuatable handles.

Figure 10:
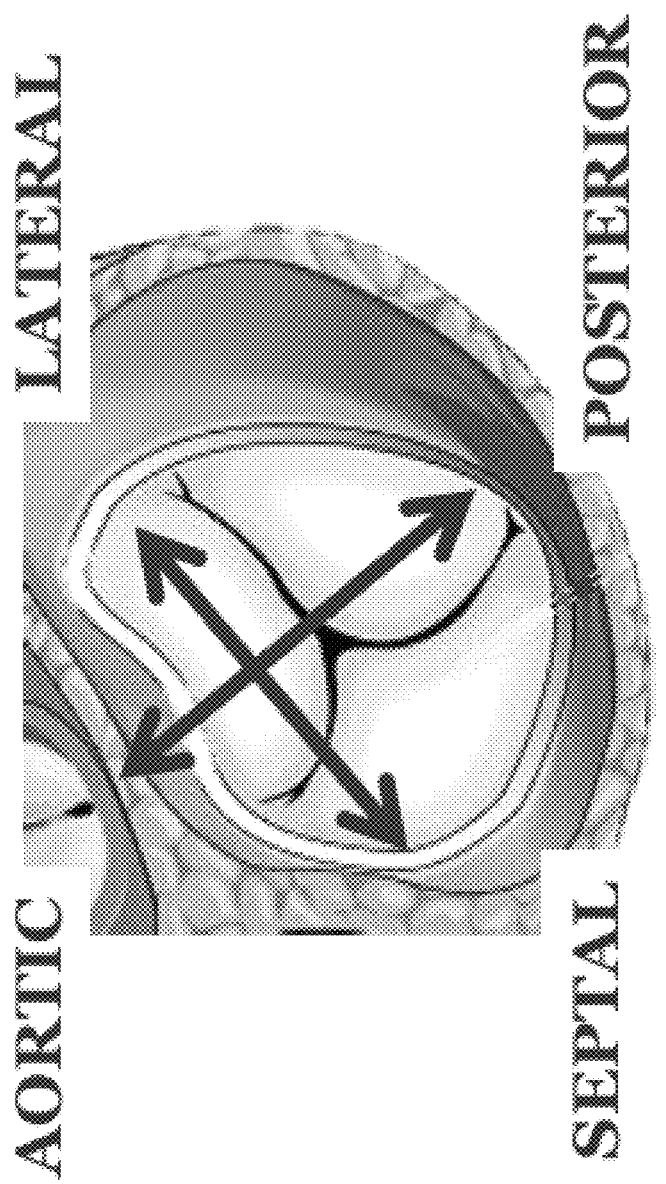
FIG. 10 is a schematic top down view of a tricuspid valve.
Figure 11:
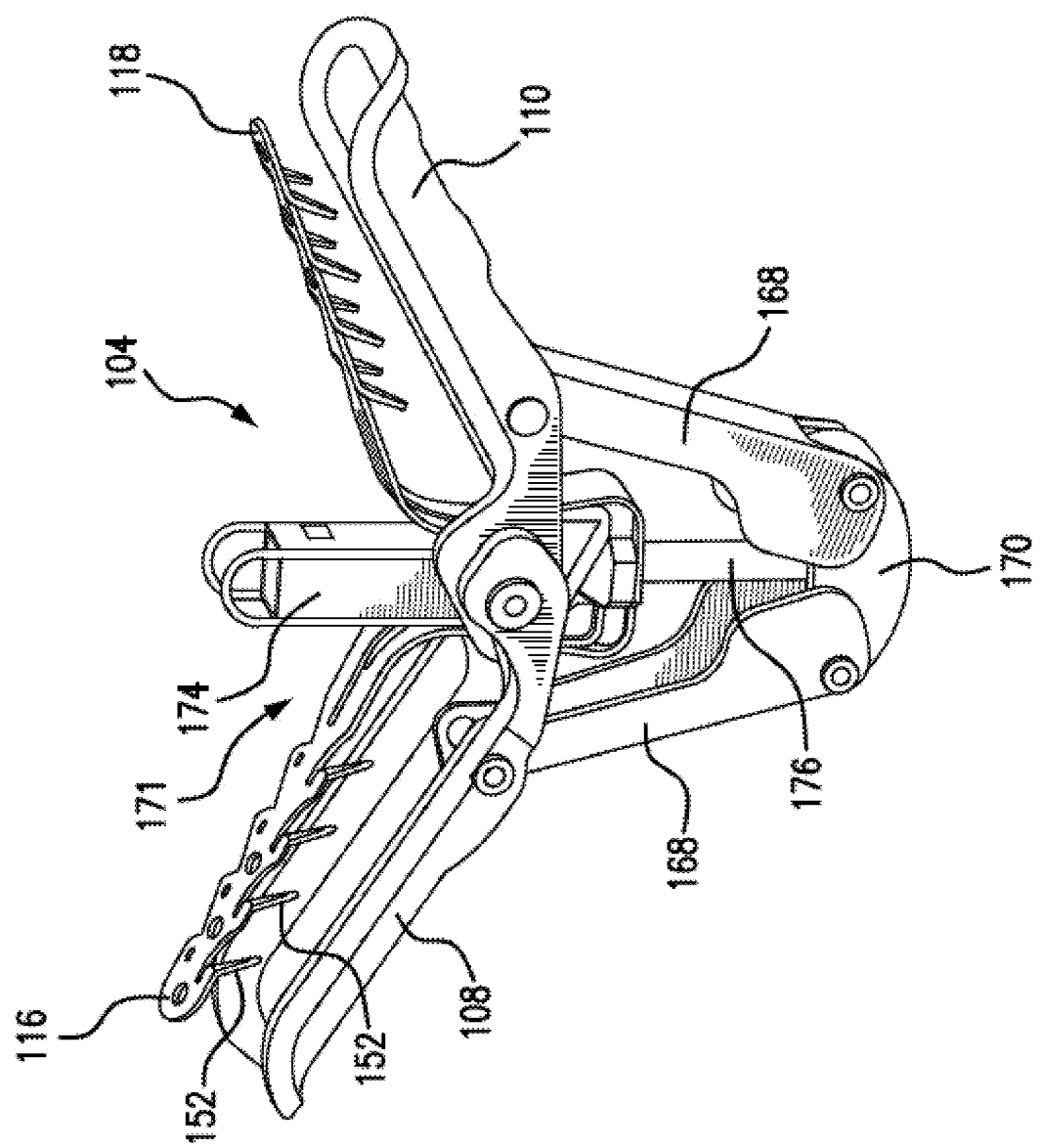
FIG. 11 is a perspective view of an exemplary embodiment of a fixation device for use in accordance with the disclosed subject matter.

Referring to FIG. 10 for purpose of illustration and not limitation, FIG. 10 provides a top-down, cut-away view of the tricuspid valve. FIG. 10 also shows the axis that will be used while describing positioning the fixation device 104 relative to the tricuspid valve. Particularly, the aortic-posterior axis includes the aortic direction, which is toward the anterior leaflet of the tricuspid valve (and the aorta) and the posterior direction, which is toward the posterior leaflet of the tricuspid valve. The septal-lateral axis includes the septal direction, which is toward the septal leaflet of the tricuspid valve and the lateral direction, which is toward the aortic-posterior commissure. In addition to being properly aligned along the aortic-posterior axis and septal-lateral axis relative to the tricuspid valve, the fixation device 104 can be positioned at the proper height relative to the tricuspid valve. As used herein, gaining height will refer to moving away from the tricuspid valve (up out of the page) and losing height will refer to moving toward the tricuspid valve (down into the page).

In operation, the medical delivery system 1 can be used to properly position the fixation device 104 relative to the tricuspid valve. To properly position the fixation device 104, steering knob 1300A, 1300B, and 1300C can be used. Additionally, all or a portion of the delivery system 1 can be advanced, and all or a portion of the delivery system 1 can be rotated. For example, positioning can be controlled by the following actions.

| Device Maneuver | Axial movement | Height Effect |
| --- | --- | --- |
| Advance entire delivery system 1 | Toward aortic direction | May gain height |
| Retract entire delivery system 1 | Toward posterior direction | May lose height |
| Steering knob 1300B clockwise (CW) | Toward septal direction | May gain height |
| Steering knob 1300B counter clock wise (CCW) | Toward lateral direction | May lose height |
| Steering knob 1300A CW | Toward posterior/septal direction | Lose height |
| Steering knob 1300A CCW | Toward aortic/septal direction | Gain height |
| Steering knob 1300C CW | Toward posterior/septal direction | Lose height |
| Steering knob 1300C CCW | Toward aortic/septal direction | Gain height |
| Rotate handle 300 CW | Toward septal direction | May gain height |
| Rotate handle 300 CCW | Toward lateral direction | May lose height |

Positioning of the fixation device 104 can be achieved with iterative adjustments of the delivery system 1 using translation (advance/retract), torque (rotating handle 300), and knob adjustments (as described above). Steering knobs 1300A, 1300C, and translation of delivery system 1 can be used as the primary movements for successful positioning. Because steering knobs 1300A and 1300C control steering through the second outer-guide catheter curve 1017B and the inner-guide catheter curve 1027, respectively, which can be co-planar, steering knobs 1300A and 1300C can be adjusted to maintain proper height and alignment, and can compensate for each other. Once the fixation device 104 is properly positioned relative to the tricuspid valve, the leaflets can be grasped, as set forth below, and the fixation device 104 can be released for implantation.

Referring to FIGS. 11-14 for purpose illustration and not limitation, an exemplary fixation device 104 for fixation of native leaflets of a heart valve is disclosed herein. The fixation device 104 as embodied herein can include a central assembly 171. The central assembly 171 can include various central components for operation and release of the fixation device 104 for example, a coupling member 174 as described in the disclosures of the patents and applications incorporated by reference herein. The fixation device 104 as depicted can include at least one arm 108 moveably coupled to the central assembly 171. As shown, the fixation device 104 can further include a second arm 110 moveably coupled to the central assembly 171.

Figure 12:
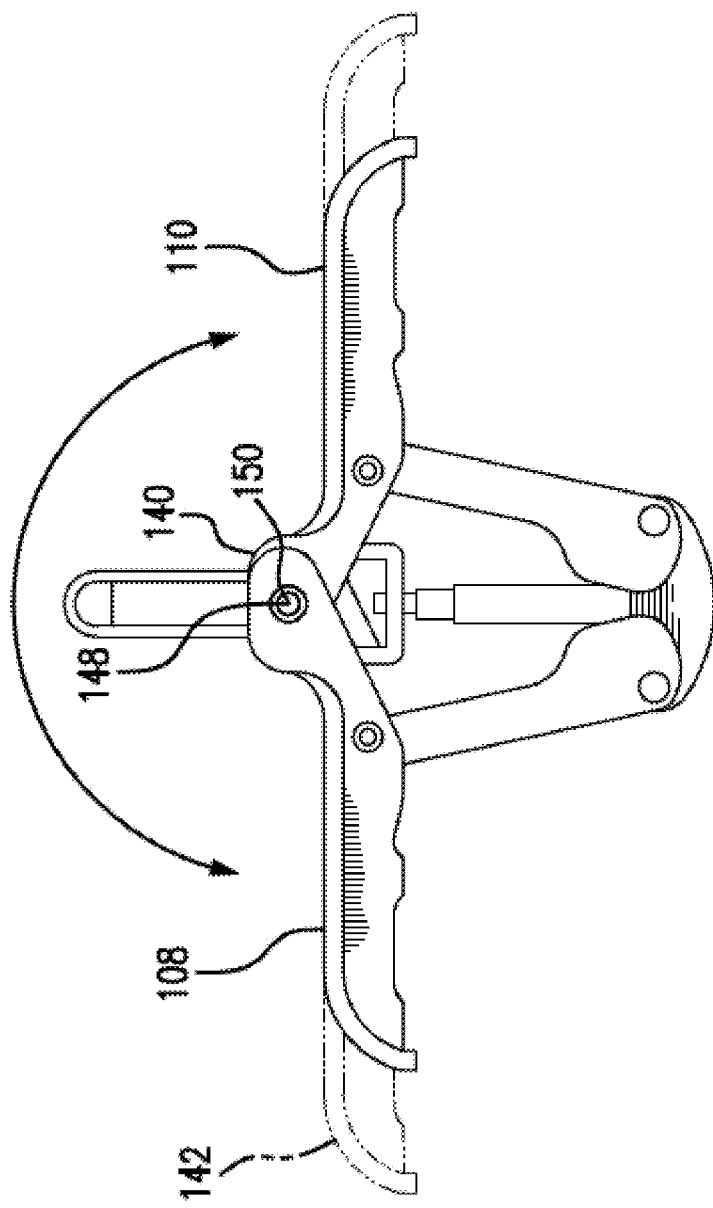
FIG. 12 is a front view of the fixation device of FIG. 11 at a different position, wherein optional arms of greater length are depicted in dashed lines.

With reference to FIG. 12, and further in accordance with the disclosed subject matter, each arm 108, 110 can be rotatable about a respective axis point 148, 150 between closed, open and inverted positions, as well as any position therebetween. Furthermore, the arms 108, 110 can be selected from a range of suitable lengths, wherein the appropriate length can be selected by the physician or health care provided, for example after inspection of a patient. For purpose of comparison, a first length of each arm 108, 110 is depicted in FIG. 12 in solid lines, and a second longer length of each arm of the disclosed subject matter is depicted in dashed lines. The arms in solid lines can be an entirely separate arm with a different length as compared to the arm in dashed lines.

As depicted herein in FIGS. 13A-13C, various positions of the fixation device 104 are depicted for purpose of illustration and not limitation. Elongated arms are illustrated in dashed lines for comparison to shorter arms (in solid lines). In FIG. 13A, the fixation device 104 is in the closed position, wherein the arms are positioned axially in alignment, e.g., vertically or nearly vertically as shown. FIGS. 13B and 13C illustrate the arms positioned with an angle A between each other. In FIG. 13B, angle A is about 10 degrees, and in FIG. 13C, angle A is about 60 degrees. As disclosed herein, the fixation device 104 is in the closed position when angle A is about 30 or less degrees. Although not depicted, the arms can continue to open until angle A exceeds 180 degrees, e.g., inverted.

The fixation device 104 can further include at least one gripping element 116 moveable relative to the at least one arm 108 to capture native leaflet therebetween. In accordance with the disclosed subject matter, each arm can be configured to define or have a trough aligned along the longitudinal axis. The trough can have a width sized greater than a width of the gripper element so as to receive the gripper element therein.

The fixation device 104 can further include a second gripping element 118 moveable relative to the second arm 110 to capture a second native leaflet therebetween. Further, in accordance with the disclosed subject matter, the at least one gripping element 116, 118 can have at least one friction element 152 along a length thereof. As embodied herein, each gripping element 116, 118 can include a plurality of friction elements 152, which can be disposed in rows. For example, each gripping element 116 and 118 can have a least four rows of friction elements 152. The friction elements 152 can allow for improved tissue engagement during leaflet capture. This gripping element design can increase the assurance that single device leaflet detachment will not occur during or after a procedure. To adjust the fixation device 104 after an initial leaflet capture, the arms can be opened, the gripping element can be raised vertically, and tissue can disengage from the fixation device 104, facilitating re-grasp and capture.

As further embodied herein, each gripping element 116, 118 can be biased toward each respective arm 108, 110. Prior to leaflet capture, each gripping element 116, 118 can be moved inwardly toward a longitudinal center of the device (e.g., away from each respective arm 108, 110) and held with the aid of one or more gripper element lines (not shown), which can be in the form of sutures, wire, nitinol wires, rods, cables, polymeric lines, or other suitable structures. The sutures can be operatively connected with the gripping elements 116, 118 in a variety of ways, such as by being threaded though loops disposed on gripping elements 116, 118.

Fixation device 104 can further include two link members or legs 168, and as embodied herein, each leg 168 has a first end rotatably joined with one of the arms 108, 110 and a second end rotatably joined with a base 170. The base 170 can be operatively connected with a stud 176 which can be operatively attached to an actuator rod 64 of the delivery system (see FIG. 9). In some embodiments, the stud 176 can be threaded such that the actuator rod 64 can attach to the stud 176 by a screw-type action. Further, the connection point between the stud 176 and the actuator rod 64 can be disposed within the coupling member 174. However, the actuator rod 64 and stud 176 can be operatively connected by any mechanism which is releasable to allow the fixation device 104 to be detached. The stud 176 can be axially extendable and retractable to move the base and therefore the legs 168, which can rotate the arms 108, 110 between closed, open and inverted positions. Immobilization of the stud, such as by a locking mechanism, can hold the legs 168 in place and therefore lock the arms 108, 110 in a desired position. Further details are disclosed in the patents and published applications incorporated by reference herein.

As previously noted, a native leaflet can be captured between each arm and respective gripping element. Each arm can then be moved toward its closed position. In this matter, adjacent leaflets can further be captured between the arms in the closed position. For example, and for illustration only, FIGS. 14A and 14B show the fixation device 104 depicted with arms 108, 110 at an angle A of about 10 to 30 degrees with two leaflets captured therebetween, wherein each leaflet is captured between an arm and a respective gripping element (gripping elements not shown). As illustrated in FIG. 14B, a contact patch area 222 depicted in dashed lines and is defined by the area of tissue captured between the arms. The contact patch area 222 can depict a tissue-to-tissue contact patch area defined by area of a leaflet in contact with a counterpart leaflet. As previously noted, FIG. 14B depicts the contact patch area 222 when the fixation device 104 is oriented at angle A of about 10 to 30 degrees.

Figure 15:
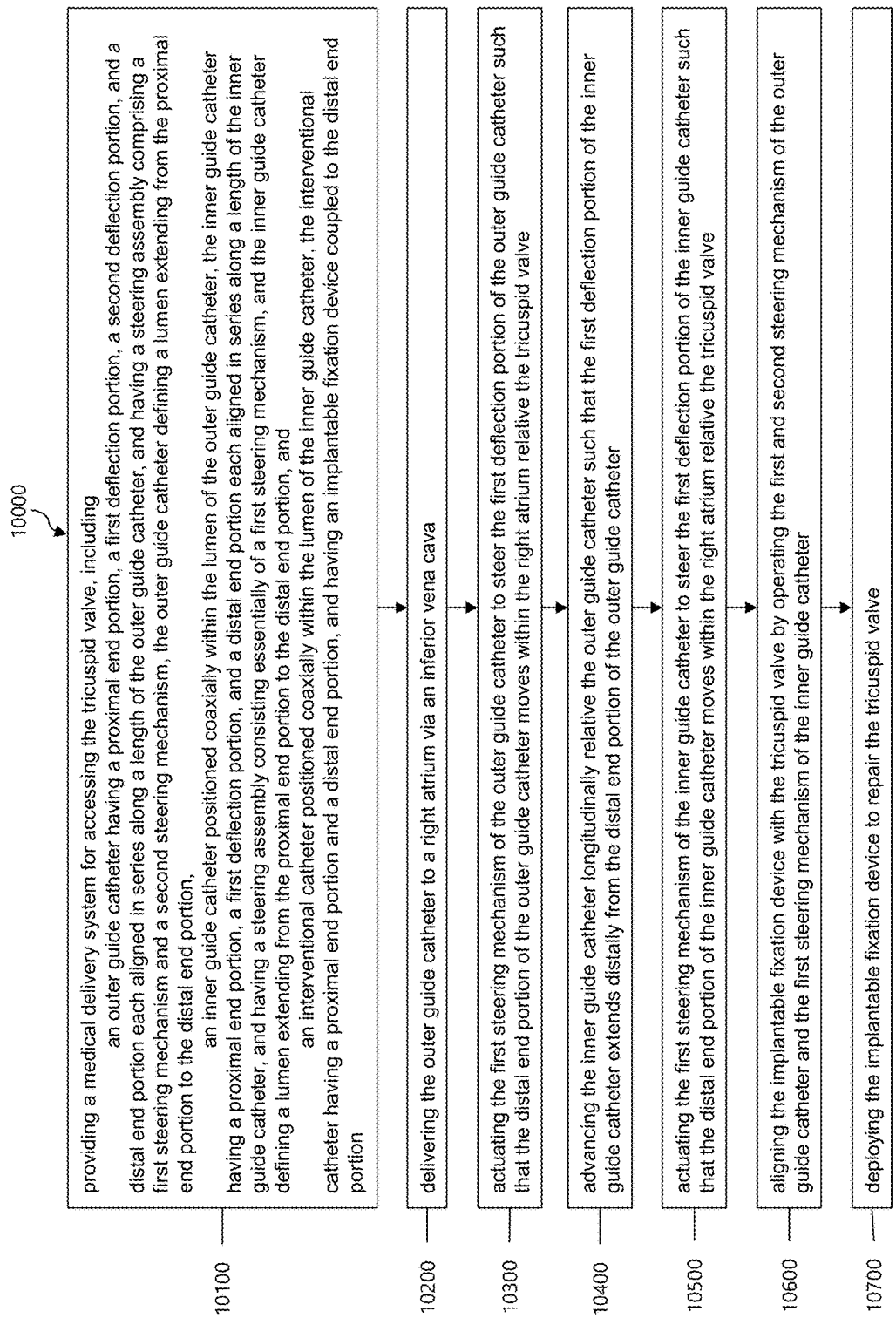
FIG. 15 is flow chart of a method of repairing a tricuspid valve in accordance with the disclosed subject matter.

FIG. 15 illustrates an exemplary method 10000 for repairing a tricuspid valve in accordance with the disclosed subject matter. The method can begin at step 10100, where the method includes providing a medical delivery system for accessing the tricuspid valve. The medical delivery system can include an outer guide catheter having a proximal end portion, a first deflection portion, a second deflection portion, and a distal end portion each aligned in series along a length of the outer guide catheter, and having a steering assembly comprising a first steering mechanism and a second steering mechanism, the outer guide catheter defining a lumen extending from the proximal end portion to the distal end portion, an inner guide catheter positioned coaxially within the lumen of the outer guide catheter, the inner guide catheter having a proximal end portion, a first deflection portion, and a distal end portion each aligned in series along a length of the inner guide catheter, and having a steering assembly consisting essentially of a first steering mechanism, and the inner guide catheter defining a lumen extending from the proximal end portion to the distal end portion, and an interventional catheter positioned coaxially within the lumen of the inner guide catheter, the interventional catheter having a proximal end portion and a distal end portion, and having an implantable fixation device coupled to the distal end portion At step 10200 the method includes delivering the outer guide catheter to a right atrium via an inferior vena cava. At step 10300 the method includes actuating the first steering mechanism of the outer guide catheter to steer the first deflection portion of the outer guide catheter such that the distal end portion of the outer guide catheter moves within the right atrium relative the tricuspid valve. At step 10400 the method includes advancing the inner guide catheter longitudinally relative the outer guide catheter such that the first deflection portion of the inner guide catheter extends distally from the distal end portion of the outer guide catheter. At step 10500 the method includes actuating the first steering mechanism of the inner guide catheter to steer the first deflection portion of the inner guide catheter such that the distal end portion of the inner guide catheter moves within the right atrium relative the tricuspid valve. At step 10600 the method includes aligning the implantable fixation device with the tricuspid valve by operating the first and second steering mechanism of the outer guide catheter and the first steering mechanism of the inner guide catheter. At step 10700 the method includes deploying the implantable fixation device to repair the tricuspid valve. In accordance with the disclosed subject matter, the method can repeat one or more steps of the method of FIG. 15, where appropriate. Although this disclosure describes and illustrates particular steps of the method of FIG. 15 as occurring in a particular order, this disclosure contemplates any suitable steps of the method of FIG. 15 occurring in any suitable order. Moreover, although this disclosure describes and illustrates an example method repairing a tricuspid valve including the particular steps of the method of FIG. 15, this disclosure contemplates any suitable method for repairing a tricuspid valve including any suitable steps, which can include all, some, or none of the steps of the method of FIG. 15, where appropriate. Furthermore, although this disclosure describes and illustrates particular components, devices, or systems carrying out particular steps of the method of FIG. 15, this disclosure contemplates any suitable combination of any suitable components, devices, or systems carrying out any suitable steps of the method of FIG. 15.

Figure 16:
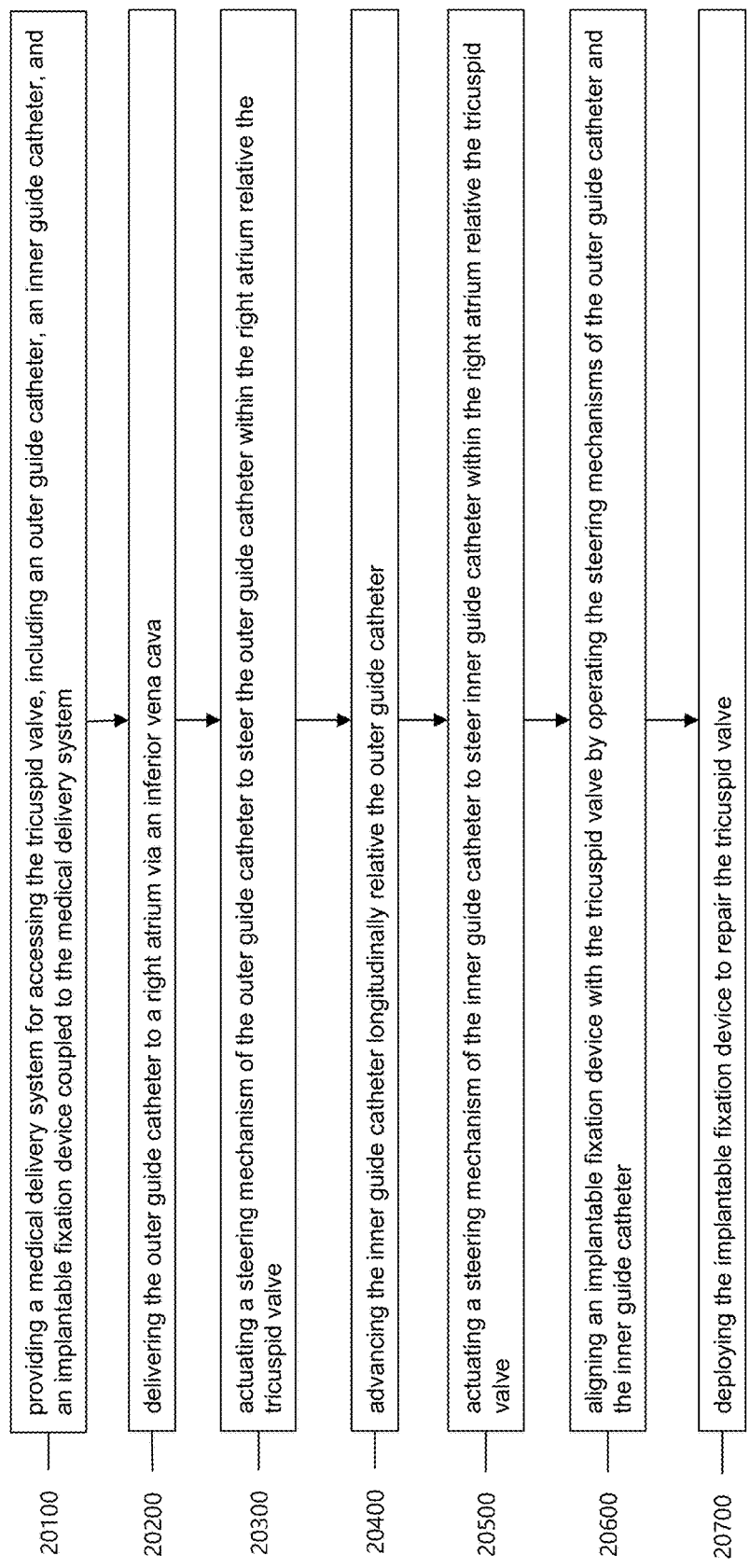
FIG. 16 is a flow chart of a method of repairing a tricuspid valve in accordance with the disclosed subject matter.

FIG. 16 illustrates an exemplary method 20000 for repairing a tricuspid valve in accordance with the disclosed subject matter. The method can begin at step 20100, where the method includes providing a medical delivery system for accessing the tricuspid valve. The medical delivery system can include an outer guide catheter, an inner guide catheter, and an implantable fixation device coupled to the medical delivery system. At step 20200 the method includes delivering the outer guide catheter to a right atrium via an inferior vena cava. At step 20300 the method includes actuating a steering mechanism of the outer guide catheter to steer the outer guide catheter within the right atrium relative the tricuspid valve. At step 20400 the method includes advancing the inner guide catheter longitudinally relative the outer guide catheter. At step 20500 the method includes actuating a steering mechanism of the inner guide catheter to steer inner guide catheter within the right atrium relative the tricuspid valve. At step 20600 the method includes aligning the implantable fixation device with the tricuspid valve by operating the steering mechanisms of the outer guide catheter and the inner guide catheter. At step 20700 the method includes deploying the implantable fixation device to repair the tricuspid valve. In accordance with the disclosed subject matter, the method can repeat one or more steps of the method of FIG. 16, where appropriate. Although this disclosure describes and illustrates particular steps of the method of FIG. 16 as occurring in a particular order, this disclosure contemplates any suitable steps of the method of FIG. 16 occurring in any suitable order. Moreover, although this disclosure describes and illustrates an example method repairing a tricuspid valve including the particular steps of the method of FIG. 16, this disclosure contemplates any suitable method for repairing a tricuspid valve including any suitable steps, which can include all, some, or none of the steps of the method of FIG. 16, where appropriate. Furthermore, although this disclosure describes and illustrates particular components, devices, or systems carrying out particular steps of the method of FIG. 16, this disclosure contemplates any suitable combination of any suitable components, devices, or systems carrying out any suitable steps of the method of FIG. 16.

While the embodiments disclosed herein utilize a push-to-open, pull-to-close mechanism for opening and closing arms it should be understood that other suitable mechanisms can be used, such as a pull-to-open, push-to-close mechanism. A closure bias can be included, for example using a compliant mechanism such as a linear spring, helical spring, or leaf spring. Other actuation elements can be used for deployment of the gripper elements.

While the disclosed subject matter is described herein in terms of certain preferred embodiments for purpose of illustration and not limitation, those skilled in the art will recognize that various modifications and improvements can be made to the disclosed subject matter without departing from the scope thereof. Moreover, although individual features of one embodiment of the disclosed subject matter can be discussed herein or shown in the drawings of one embodiment and not in other embodiments, it should be readily apparent that individual features of one embodiment can be combined with one or more features of another embodiment or features from a plurality of embodiments.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other possible combinations. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

The invention claimed is:

1. A medical delivery system for accessing a tricuspid valve via an inferior vena cava, comprising
 an outer guide catheter having a proximal end portion, a first deflection portion, a second deflection portion, and a distal end portion each aligned in series along a length of the outer guide catheter, and having a steering assembly comprising a first steering mechanism and a second steering mechanism, the outer guide catheter defining a lumen extending from the proximal end portion to the distal end portion;
an inner guide catheter positioned coaxially within the lumen of the outer guide catheter, the inner guide catheter having a proximal end portion, a first deflection portion, and a distal end portion each aligned in series along a length of the inner guide catheter, and having a steering assembly consisting essentially of a first steering mechanism, and the inner guide catheter defining a lumen extending from the proximal end portion to the distal end portion;
an interventional catheter positioned coaxially within the lumen of the inner guide catheter, the interventional catheter having a proximal end portion and a distal end portion, and having an implantable fixation device coupled to the distal end portion;
wherein the first deflection portion of the outer guide catheter is steerable to define a first outer-guide-catheter curve and the second deflection portion of the outer guide catheter is steerable to define a second outer-guide-catheter curve; and
the first deflection portion of the inner guide catheter is steerable to define a first inner-guide-catheter curve having a radius up to approximately 0.510 inches.

2. The system of claim 1, wherein the first steering mechanism of the outer guide catheter is configured to steer the first deflection portion of the outer guide catheter, and the second steering mechanism of the outer guide catheter is configured to steer the second deflection portion of the outer guide catheter.

3. The system of claim 2, wherein at least one of the first outer-guide-catheter curve and the second outer-guide-catheter curve is preformed in the outer guide catheter.

4. The system of claim 2, wherein the second outer-guide-catheter curve is preformed in the outer guide catheter.

5. The system of claim 2, wherein the first outer-guide-catheter curve and the second outer-guide-catheter curve are preformed in the outer guide catheter.

6. The system of claim 1, wherein the first steering mechanism of the inner guide catheter is configured to steer the first deflection portion of the inner guide catheter.

7. The system of claim 6, wherein the first inner-guide-catheter curve is preformed in the inner guide catheter.

8. The system of claim 1, wherein the second outer-guide-catheter curve is in a first plane and the first inner-guide-catheter curve is in a second plane.

9. The system of claim 8, wherein the first plane and the second plane are the same plane.

10. The system of claim 1, wherein the implantable fixation device comprises:
a first arm and a second arm;
a first proximal element moveable relative the first arm between a first position and a second position; and
a second proximal element moveable relative to the second arm between a first position and a second position.

11. The system of claim 1, wherein the first inner-guide-catheter curve has a relaxed state angled between approximately 40 and 50 degrees relative to a distal end of the proximal end portion of the inner guide catheter.

12. The system of claim 1, wherein the first inner-guide-catheter is steerable at an angle between approximately 0 degrees and 90 degrees relative to a distal end of the proximal end portion of the inner guide catheter.

13. A method of repairing a tricuspid valve, comprising:
providing a medical delivery system for accessing the tricuspid valve, including
an outer guide catheter having a proximal end portion, a first deflection portion, a second deflection portion, and a distal end portion each aligned in series along a length of the outer guide catheter, and having a steering assembly comprising a first steering mechanism and a second steering mechanism, the outer guide catheter defining a lumen extending from the proximal end portion to the distal end portion,
an inner guide catheter positioned coaxially within the lumen of the outer guide catheter, the inner guide catheter having a proximal end portion, a first deflection portion which is steerable to define a first inner-guide catheter curve having a radius up to approximately 0.510 inches, and a distal end portion each aligned in series along a length of the inner guide catheter, and having a steering assembly consisting essentially of a first steering mechanism, and the inner guide catheter defining a lumen extending from the proximal end portion to the distal end portion, and
an interventional catheter positioned coaxially within the lumen of the inner guide catheter, the interventional catheter having a proximal end portion and a distal end portion, and having an implantable fixation device coupled to the distal end portion;
delivering the outer guide catheter to a right atrium via an inferior vena cava;
actuating the first steering mechanism of the outer guide catheter to steer the first deflection portion of the outer guide catheter such that the distal end portion of the outer guide catheter moves within the right atrium relative the tricuspid valve;
advancing the inner guide catheter longitudinally relative the outer guide catheter such that the first deflection portion of the inner guide catheter extends distally from the distal end portion of the outer guide catheter;
actuating the first steering mechanism of the inner guide catheter to steer the first deflection portion of the inner guide catheter such that the distal end portion of the inner guide catheter moves within the right atrium relative the tricuspid valve;
aligning the implantable fixation device with the tricuspid valve by operating the first and second steering mechanism of the outer guide catheter and the first steering mechanism of the inner guide catheter; and
deploying the implantable fixation device to repair the tricuspid valve.

14. The method of claim 11, wherein the first deflection portion of the outer guide catheter is steerable to define a first outer-guide-catheter curve and the second deflection portion of the outer guide catheter is steerable to define a second outer-guide-catheter curve.

15. The method of claim 13, wherein the first outer-guide-catheter curve is in a first plane and the first inner-guide-catheter curve is in a second plane.

16. The method of claim 14, where in the first plane and the second plane are the same plane.

17. The method of claim 11, wherein the implantable fixation device comprises:
a first arm and a second arm;
a first proximal element moveable relative the first arm between a first position and a second position; and a second proximal element moveable relative to the second arm between a first position and a second position.

18. The method of claim 13, wherein the first inner-guide-catheter curve has a relaxed state angled between approximately 40 and 50 degrees relative to a distal end the proximal end portion of the inner guide catheter.

19. The method of claim 13, further comprising steering the first inner-guide-catheter at an angle between approximately 0 and 90 degrees relative to a distal end of the proximal end portion of the inner guide catheter.

* * * * *